(12) United States Patent
Hodson et al.

(10) Patent No.: US 11,707,584 B2
(45) Date of Patent: Jul. 25, 2023

(54) INHALER FLOW CONTROL MECHANISM

(71) Applicant: KINDEVA DRUG DELIVERY L.P., St. Paul, MN (US)

(72) Inventors: Peter D. Hodson, Derbyshire (GB); Stephen J. Howgill, Leicestershire (GB)

(73) Assignee: Kindeva Drug Delivery L.P., Woodbury, MN (US)

( * ) Notice: Subject to any disclaimer, the term of this patent is extended or adjusted under 35 U.S.C. 154(b) by 933 days.

(21) Appl. No.: 16/609,234

(22) PCT Filed: Apr. 30, 2018

(86) PCT No.: PCT/US2018/030088
§ 371 (c)(1),
(2) Date: Oct. 29, 2019

(87) PCT Pub. No.: WO2018/204217
PCT Pub. Date: Nov. 8, 2018

(65) Prior Publication Data
US 2020/0069897 A1 Mar. 5, 2020

(30) Foreign Application Priority Data
May 4, 2017 (GB) ..................... 1707095

(51) Int. Cl.
*A61M 15/00* (2006.01)
(52) U.S. Cl.
CPC ............... *A61M 15/0093* (2014.02)

(58) Field of Classification Search
CPC ..................... A61M 15/0091–0096
See application file for complete search history.

(56) References Cited

U.S. PATENT DOCUMENTS

| | | | |
|---|---|---|---|
| 5,161,524 A | 11/1992 | Evans | |
| 5,988,163 A | 11/1999 | Casper | |
| 2004/0099266 A1 | 5/2004 | Cross | |
| 2008/0017189 A1 | 1/2008 | Ruckdeschel et al. | |
| 2011/0114089 A1* | 5/2011 | Andersen | A61M 15/0081 128/200.23 |
| 2011/0155129 A1 | 6/2011 | Stedman | |
| 2012/0055467 A1 | 3/2012 | Brambilla | |

(Continued)

FOREIGN PATENT DOCUMENTS

| | | |
|---|---|---|
| WO | 2016/001926 | 1/2016 |
| WO | WO 2017-112400 | 6/2017 |

(Continued)

OTHER PUBLICATIONS

International Search report for International Application No. PCT/US2018/030088 dated Jul. 6, 2018, 3 pages.

(Continued)

*Primary Examiner* — Rachel T Sippel
(74) *Attorney, Agent, or Firm* — Mueting Raasch Group

(57) ABSTRACT

An inhaler (60) has a breath actuated trigger mechanism (100) reactive to an inhalation flow to trigger the release of a substance to be inhaled. The inhaler (60) has an inspiration flow which is subject to a higher degree of flow governing post-triggering than pre-triggering. This allows the triggering flow rate to be closer to, or even higher than, the governing flow rate of the inhaler.

15 Claims, 22 Drawing Sheets

(56) References Cited

U.S. PATENT DOCUMENTS

| | | |
|---|---|---|
| 2013/0037021 A1 | 2/2013 | Brewer |
| 2014/0116426 A1 | 5/2014 | Mullinger |
| 2018/0369512 A1 | 12/2018 | Blatchford |
| 2019/0001081 A1 | 1/2019 | Guion |
| 2019/0001085 A1 | 1/2019 | Cottenden |

FOREIGN PATENT DOCUMENTS

| | | |
|---|---|---|
| WO | WO 2017-112452 | 6/2017 |
| WO | WO 2017-112748 | 6/2017 |
| WO | WO 2018-048797 | 3/2018 |

OTHER PUBLICATIONS

Japanese Office Action for JP 2019-560127 issued by the Japanese Patent Office dated Oct. 14, 2021 (dated Oct. 19, 2021); 4 pgs. including English Translation.

Extended European Search Report issued for EP Application No. 18794444.2, dated Dec. 16, 2020; 8 pgs.

* cited by examiner

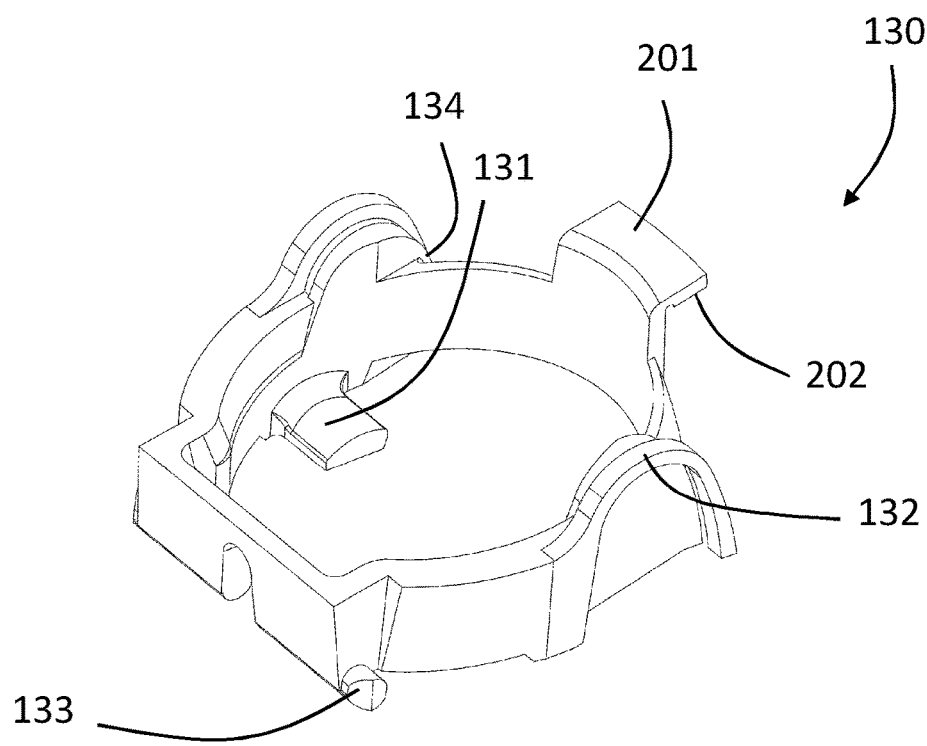
Fig. 14
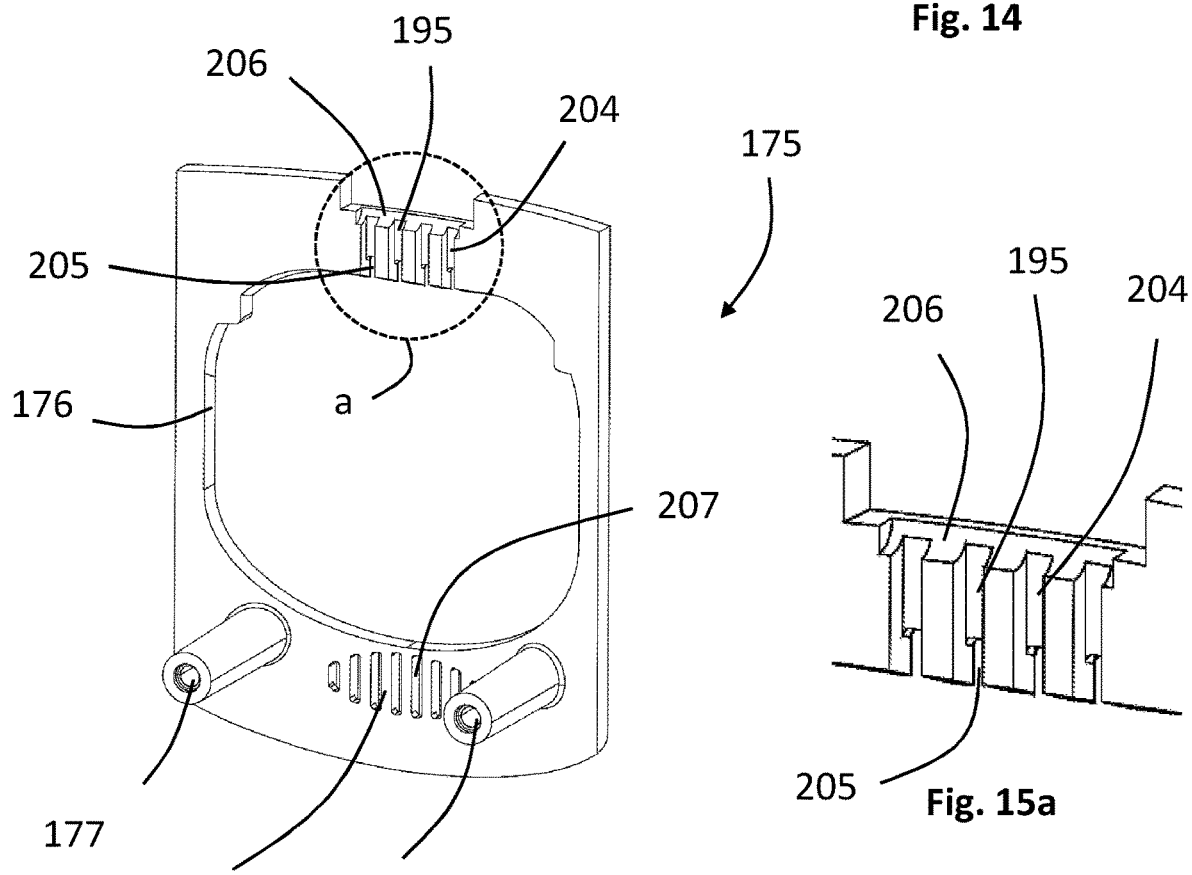
Fig. 15  Fig. 15a

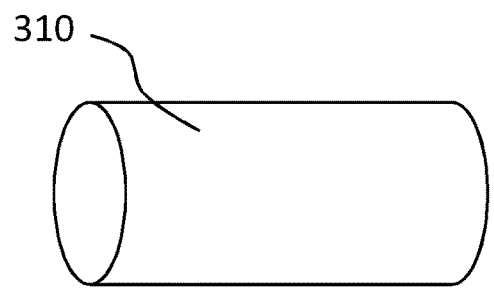
Fig. 21a
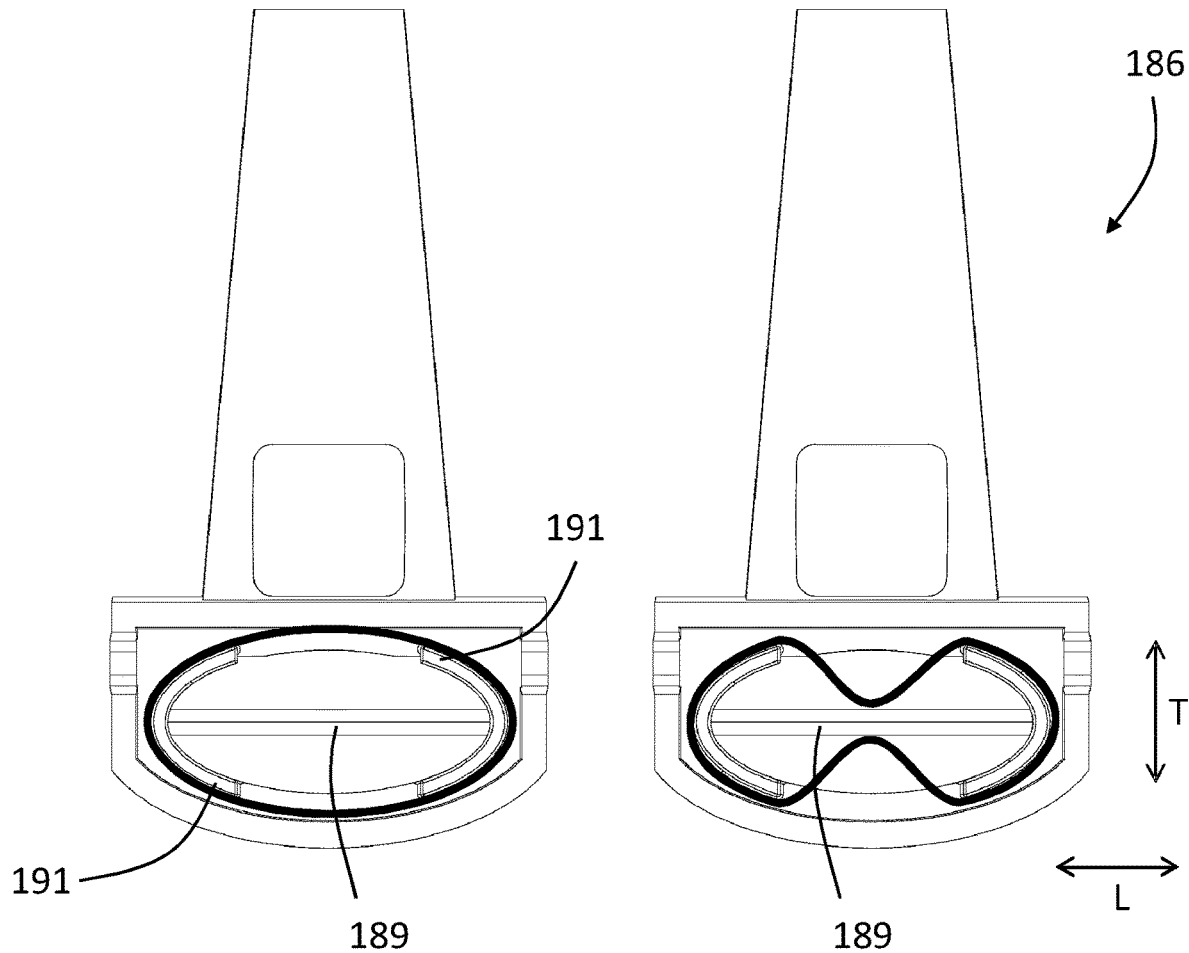
Fig. 21b
Fig. 21c

INHALER FLOW CONTROL MECHANISM

CROSS REFERENCE TO RELATED APPLICATIONS

This application is a national stage filing under 35 U.S.C. 371 of PCT/US2018/030088, filed Apr. 30, 2018, which claims the benefit of United Kingdom Patent Application No. GB1707095.4, filed 4 May 2017, the disclosure of which is incorporated by reference in its entirety herein.

FIELD

The present application concerns a flow control mechanism for inhalers, in particular breath-actuated medicinal inhalers. The application also relates to inhalers, and in particular to medicinal inhalers containing such flow control mechanisms.

RELATED APPLICATIONS

The invention described herein is well suited to implementation in the type of inhalers described in the applicant's PCT Publication No. WO2018/048797. This document is therefore incorporated by reference where permitted.

BACKGROUND

Delivery of aerosolized medicament to the respiratory tract for the treatment of respiratory and other diseases is conventionally done using inhalers of either the pressurised metered dose inhaler (pMDI), the dry powder inhaler (DPI) or the nebulizer type. pMDI inhalers in particular have become an industry standard, and are familiar to many patients who suffer from either asthma or from chronic obstructive pulmonary disease (COPD). Conventional pMDI devices comprise a canister comprising an aluminium container sealed with a metering valve. The container contains the medicament formulation. Generally, the medicament formulation is a pressurized formulation containing either fine particles of one or more medicinal compounds suspended in a liquefied hydrofluoroalkane (HFA) propellant, or a solution of one or more medicinal compounds dissolved in a propellant/co-solvent system. Other excipients may be included, e.g. surfactant, acid to act as a stabilizer, bulking agent. Formulations incorporating one drug in solution and another one in suspension form are also known.

In a conventional pulmonary pMDI, the sealed canister is provided to the patient in an actuator. The actuator is conventionally a generally L-shaped plastic moulding comprising a generally cylindrical vertical tube that surrounds the canister plus a generally horizontal tube that forms a patient portion (e.g., a mouthpiece or nosepiece) that defines an inspiration (or inhalation) orifice. To use such an inhaler, the patient exhales, places the patient port into a body cavity (e.g., a mouth or nose) and then inhales to draw air through the inspiration orifice. (For nasal drug delivery, inhalation might not be required.) The majority of such inhalers are of the pulmonary "press-and-breathe" type, where the patient must press down on the protruding end of the canister in order to operate the metering valve to release a metered dose of medicament from the canister into the inhaled air stream and thence through the mouthpiece into their lungs. This requires a significant degree of coordination of timing of inhalation and dose release if the emerging cloud of aerosolized medicament is to be taken far enough into the lungs to provide maximum therapeutic benefit. If the patient releases the dose before inspiratory flow has been established, then a proportion of the drug is likely to be lost in the mouthpiece or the patient's mouth. Conversely, if released much after the start of inhalation, then the deeper regions of the lungs might already be full of air and not penetrated by the following bolus of released medicament aerosol.

Spacer devices have previously been devised which fit onto the mouthpiece of a pMDI in order to reduce the velocity of the emergent plume of medicament aerosol and to provide a volume in which it can expand and its propellant can evaporate more completely. This serves to avoid some of the problems of coordination and also avoids the tendency for high throat deposition caused by excessively fast drug particle inhalation. However, spacer devices are very bulky, and they can retain an excessive proportion of the drug on their walls, thereby reducing the dose that reaches the patient. Spacer devices can also be highly sensitive to electrostatic charge, which can often be strongly affected by the way in which they are washed or dried.

To overcome what can be quite a challenge for some patients, pMDI device designs have been created that employ automatic breath-actuated triggering mechanisms, releasing a dose only in response to the patient's inhaled breath. Typically, an energy storage means is provided which is primed by the user (for example by compressing a spring) and released by the triggering mechanism to provide an actuation load upon the canister and thereby release the medicament. Once triggered, the inhaler needs to be reset for the next operation by a reset mechanism.

The AUTOHALER™ metered dose inhaler, available from 3M Company, St. Paul, Minn., USA and the EASI-BREATHE™ inhaler, available from Teva Pharmaceutical Industries Ltd., Israel, are two such pMDI devices that use breath-actuation to attempt to better coordinate dose release with inhalation. Many other inhaler breath-actuated mechanisms and reset mechanisms have been proposed, but tend to have one or more weaknesses or disadvantages.

Even though breath-actuated inhalers can be a useful aid in achieving coordination between inhalation and medicament dose release, with consequently improved medicament delivery to many patients' lungs, these devices are unable to overcome all the potential weaknesses that patients can exhibit in their inhaler use technique. For example, even if patients can achieve good timing of dose release, whether via breath-actuation or simply via good press-and-breathe coordination, they can have a tendency to inhale at sub-optimal flow rates. For example, very high inspiratory flow rates (i.e., volumetric flow rates) can give rise to excessive and problematic drug deposition on the back of the throat, while very low inspiratory flow rates can lead to poor entrainment of the aerosolized medicament spray. A related additional potential problem is that very high inspiratory flow rates can lead to more rapid filling of the lungs and consequently an even greater need for good coordination.

As a result of poor inhalation and dose release coordination, many patients do not get the full therapeutic benefit of their medicinal inhalers. For example, many patients with uncontrolled asthma are unable to (i) achieve a flow rate between 10 to 50 litres/minute (L/min.); (ii) maintain the flow rate for at least 1.5 seconds; and (iii) hold their breath for at least 5 seconds after inspiration. Poor inhaler use technique has been found to correlate with poor control of asthma in particular.

Because the manner in which patients inhale through their pMDIs is an important determinant of the delivery of drug to their lungs, it is desirable for all patients to inhale in a similar and consistent manner. The general view in the guidance provided by pharmaceutical companies is that pMDI medications should be taken with patients taking a slow and deep inhalation, normally interpreted as being less than 50-60 L/min.

For conventional pMDIs and other inhalers, however, inhalation flow rate control varies from one user to another and even from one breath to another for the same patient. Some patients can sometimes achieve flow rates as high as 250 L/min., while others can sometimes achieve an order of magnitude less. Inhaling the medicament at a lower flow rate tends to reduce drug impaction in the upper airways and increases drug deposition deeper in the lung. If a patient is unable to control their asthma, or any other respiratory disease requiring use of an inhaler, this will impact their quality of life and may lead to the requirement for further medical intervention. This is clearly unfavourable.

Inhaler designs each have their own inherent resistance (R) to air flow. This is often expressed in the units $(Pa)^{0.5}$ (min./L), and is related to inhalation air flow rate (FR) and patient-created pressure drop (PD) by the equation:

$$R = \frac{PD^{0.5}}{FR}$$

Existing pMDI inhalers usually have low inherent resistances to air flow, for example below 0.5 $(Pa)^{0.5}$ (min./L), which makes it difficult for patients to control their inhalation flow rate. Breathing profiles can be too rapid. Breath-dosing coordination can be difficult under such circumstances, and both the inter-patient and intra-patient variability can be high. With resistances of this order it can also be difficult for patients to achieve a steady flow rate of a duration of more than e.g. 2 to 2.5 seconds. Flow rate consistency during an inspiratory manoeuvre, and between inhalations, can be difficult to obtain. For example, flow rate "spikes" can occur, whereby patients achieve fairly high but very transient flow rates. This can lead to poor spatial distributions of drug in their airways.

One solution is to increase the inhaler's resistance to flow (i.e. increase R). However, adding a significant fixed ("static") resistance to the design of a pMDI device also poses problems. By restricting the geometry of the air flow path in an inhaler, much higher resistances could be created, for example 1.6 $(Pa)^{0.5}$ (min./L) or more. Such resistances are typical of some DPI devices, where a high resistance is required to generate the energy needed to disperse and/or de-agglomerate a dose of medicament powder from a system without the energy content of a liquefied propellant. Unfortunately, though, while high resistances make it much easier for many patients to inhale more slowly and steadily through an inhaler, and for a longer period (e.g., 5 seconds or more), they pose an obstacle to some weaker patients who struggle to inhale adequate amounts of air against such a resistance. COPD patients, in particular, often find it difficult to inhale through such high resistances because of their impaired lung function.

In order to overcome some of the above-described issues related to either a low or a high inhaler resistance, while also avoiding the need for a spacer device, flow governors and flow governor assemblies have been developed, e.g., as described in PCT Publication Nos. WO2017/112748; WO2017/112452 and WO2017/112400. These flow governors have the ability to change their geometry and resistance to air flow as a function of the pressure drop experienced, i.e., between an inlet and outlet of the flow governor. Flow governors (which can also be referred to as "flow rate limiters," "flow limiters," "flow regulators," "flow limitation devices," or derivations thereof) allow appreciable air flow rates at low differential pressures, while increasing air flow resistance at higher differential pressures in order to limit the air flow rates to values more consistent with those obtained at lower differential pressures to reduce inter-patient and intra-patient inhalation variability.

Sophisticated pMDI inhalers have been proposed that incorporate both a breath-actuated dose release triggering system and also a flow governor system. In such an inhaler, it is important that the air flow rate to which the flow governor restricts the air flow is greater in any individual inhaler (and any individual inhalation event) than the air flow rate at which the breath-actuation system triggers. If that is not the case, then there is the potential for the flow governor to prevent the air flow through the inhaler from ever reaching that required to trigger the release of a dose of medicament. This would be clearly problematic in triggering medicament release.

To avoid that scenario, such inhalers might beneficially be arranged to have a clear difference between their triggering flow rate (TFR) and their governing flow rate (GFR). For example, they might be specified to have a TFR of 15±5 L/min. and a GFR of 30±5 L/min., meaning that at "worst case" there would be at least 5 L/min. between the maximum possible TFR of 20 L/min. and the minimum possible GFR of 25 L/min. However, such specifications are less than perfect, as they mean that GFR might have to be set unfavourably high and that TFR might have to be set unstably low. Additionally, even with such a gap between specifications, there is still the potential concern that out-of-specification circumstances might arise from time to time.

It is an aim of the present invention to overcome, or at least mitigate, one or more of these problems.

SUMMARY

According to a first aspect of the present invention there is provided an inhaler comprising:

a breath actuated trigger mechanism reactive to an inhalation flow to trigger the release of a substance to be inhaled into the inhalation flow;

a first fluid flow path within the inhaler carrying part of the inhalation flow;

a flow governor arranged to govern inhalation flow through the first fluid flow path; and, a second fluid flow path within the inhaler carrying part of the inhalation flow, the second fluid flow path bypassing the flow governor;

in which triggering the trigger mechanism reduces or blocks flow through the second fluid flow path.

Advantageously, this configuration allows the TFR to be made closer to, or even greater than, the GFR. Both flow paths contribute to the inhalation flow pre-trigger, and as such allow a high TFR, a proportion of which is ungoverned. Closure (or partial closure) of the second flow path increases the proportion of the inhalation flow which is governed (up to 100%) which means that the GFR can be selected independently of the TFR.

Preferably the second flow path is at least partially blocked by a part of the trigger mechanism after triggering. By using an existing component of the mechanism which already carried out a function, the invention can be implemented with the minimum of cost and design change.

For example, the trigger mechanism may comprise an actuation member configured to support a canister in a pre-triggered position, which actuation member moves to a post-triggered position upon triggering to thereby at least partially block the second flow path.

The actuation member may define a valve member, and the inhaler may comprise a valve seat for the second flow path, in which in the pre-triggered position of the actuation member the valve member and valve seat are spaced apart, and in the post-triggered position the valve member abuts the valve seat. This takes advantage of a component that already moves during the triggering operation.

Preferably the inhaler defines a direction of actuation for a canister, the valve seat faces a direction opposite to the direction of actuation, and the valve member moves in the direction of actuation to abut the valve seat. Preferably the valve member and valve seat are shaped to as to mate upon engagement; for example, the valve member may be convex, and the valve seat may be concave. Advantageously, this allows self-alignment of the components to form a good seal to block the flow to the extent desired.

Preferably the trigger mechanism comprises a toggle mechanism for selectively permitting movement of the actuation member from its pre-triggered position to its post-triggered position. The toggle mechanism may comprise a vane positioned in the inhalation flow, the vane being moveable upon inhalation of a user to move the toggle mechanism between a primed condition in which the actuation member is maintained in its pre-triggered position by cooperation with the toggle mechanism and its post-triggered condition in which the toggle mechanism permits movement of the actuation member.

Preferably the actuation member is an actuation arm that is pivotable about a pivot axis. In this case, it is preferable that the actuation arm is configured to at least partially block the second flow path at a position on the opposite side of the canister to the pivot axis. This allows the maximum range of motion to clear the valve seat in the pre-triggered position.

Preferably the first flow path has a first flow inlet defined on the inhaler, and the second flow path has a second flow inlet defined on the inhaler, distinct from the first. Preferably the first and second flow inlets are adjacent the flow outlet. The first and second flow inlets may be on opposites sides of the flow outlet. The inhaler may comprise a cover member configured to selectively cover the first and second flow inlets and the flow outlet.

Preferably the trigger mechanism is positioned downstream of the second flow path. Preferably the trigger mechanism when it triggers reduces or blocks flow through the second fluid flow path upstream of a canister outlet. This prevents the valve being clogged or rendered less effective by medicament.

Both flow paths contribute to the inhalation flow pre-trigger, and as such allow a high TFR, a proportion of which is ungoverned. Closure (or partial closure) of the second flow path increases the proportion of the total inhalation flow which is governed (up to 100%), which means that the GFR can be selected independently of the TFR.

According to a second aspect of the invention, there is provided an inhaler comprising:
 a breath actuated trigger mechanism reactive to an inhalation flow to trigger the release of a substance to be inhaled into the inhalation flow, the breath actuated trigger mechanism comprising a vane that is responsive to inhalation flow;
 a flow governor configured to govern at least part of the inhalation flow, the flow governor having a first condition and a second condition, in which in the second condition the flow governor is capable of governing a larger flow area than in the first condition;
 in which actuation of the vane changes the flow governor from the first condition to the second condition.

Advantageously, at least partially inhibiting the action of the flow governor pre-triggering means that there is a larger portion of the flow which is ungoverned before triggering. As with the first aspect, this configuration allows the TFR to be made closer to, or even greater than, the GFR.

Preferably the flow governor comprises a flow governing member in which:
 in the second condition the flow governing member can move in reaction to flow therepast; and,
 in the first condition movement of the flow governing member is constrained.

Preferably in the first condition movement of the flow governing member is prevented (i.e. fully constrained).

Preferably the flow governing member is pivotable relative to a sidewall of a flow path, in which case in the first condition the flow governing member may be held in an open position in which it (or part of it) bears against the sidewall.

Preferably the vane has a rest position and the inhaler comprises an arm connected for movement with the flow governing member, in which the vane in the rest position constrains movement of the arm, and upon actuation away from the rest position permits movement of the arm.

Preferably the inhaler comprises a flow inlet leading to a flow governor passageway and a flow outlet leading from an inhalation flow passageway, in which the flow governor passageway and the inhalation flow passageway are adjacent.

Preferably the vane is pivotably mounted at a first end, and comprises a free end opposite the first end, in which in a rest condition of the vane, the free end is adjacent to the flow governor passageway.

BRIEF DESCRIPTION OF THE DRAWINGS

FIGS. 12 to 17 are perspective views of third to eighth parts of the subassembly of FIG. 6.

FIG. 21a is a perspective view of a flow governor component used in the pMDI inhaler of FIG. 2;

FIGS. 21b and 21c are end views of a flow governor support component of the pMDI inhaler of FIG. 2 assembled with the flow governor component of FIG. 21a;

DETAILED DESCRIPTION

Prior Art

Figure 1:
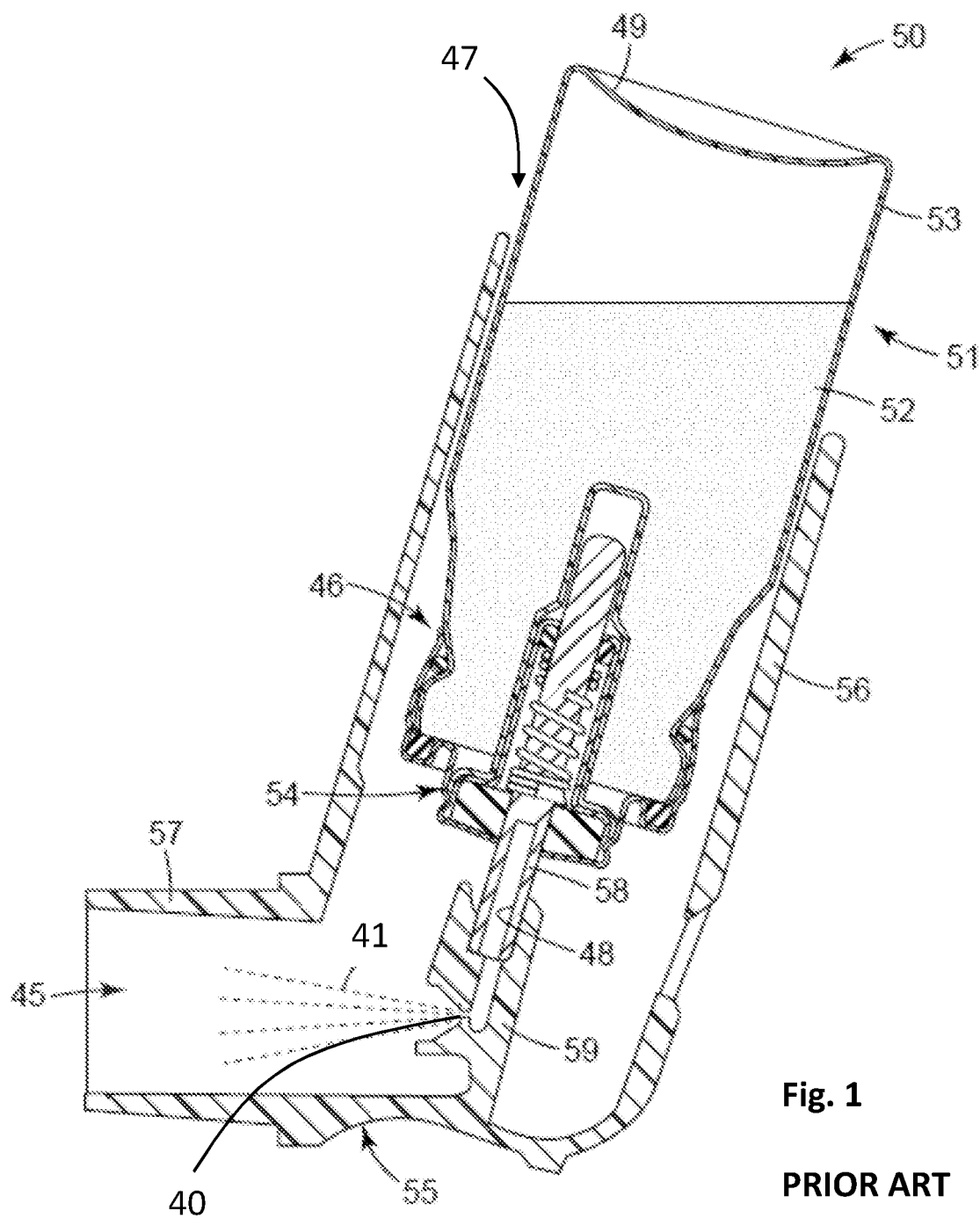
FIG. 1 is a side section view of a prior art pMDI inhaler.

FIG. 1 illustrates a conventional pressurized metered dose inhaler (pMDI) 50 comprising a valved container in the form of a canister 51 containing a medicament formulation 52, the canister comprising a can 53 sealed at a crimp 46 with a metering valve 54. The canister 51 sits within a housing (or "actuator") 55 comprising a tubular sleeve portion 56 having an open end 47 dimensioned to receive the canister 51 and from which its base 49 can protrude, and a portion in the form of a patient port 57 (e.g., in the form of a mouthpiece) that defines an inspiration orifice (or an air outlet) 45. Such a patient port of an inhaler is sometimes referred to herein as a "mouthpiece" for simplicity. However, it should be understood that such mouthpieces can instead be configured to be nosepieces of nasal inhalers and that the present disclosure can equally apply to nasal inhalers even where not specifically mentioned herein. The open upper end 47 of the housing 55 can define an aspiration orifice, or an air inlet, and the air outlet 45 can define an inhalation orifice, or an air outlet.

A stem portion 58 protrudes from the metering valve 54 and is located and retained by friction in a stem socket 59 formed as an integral part of the housing 55. A spray orifice 40 is formed in the stem socket 59, and provides a passage for fluid communication between the valve stem portion 58 and the inspiration orifice 45. In use, a patient places the patient port (e.g., mouthpiece) 57 into a body cavity (e.g., mouth) and then inhales through it while at the same time pressing downwards on the protruding base 49 of the canister 51. The pressing force serves to move the canister 51 downwards relative to the valve's stem portion 58. That relative movement serves to isolate a metered dose of medicament formulation from the bulk formulation in the canister 51 and then to discharge it via a hollow bore 48 formed in the stem portion 58. The discharged dose then passes along the fluid passageway through the stem socket 59 and emerges via a spray orifice in the form of a fine respirable spray 41 that passes through the patient port 57 into the patient's body cavity (e.g., oral cavity and/or nasal cavity) and thence into their respiratory passages, thereby treating their disease.

The First Embodiment

Figure 2:
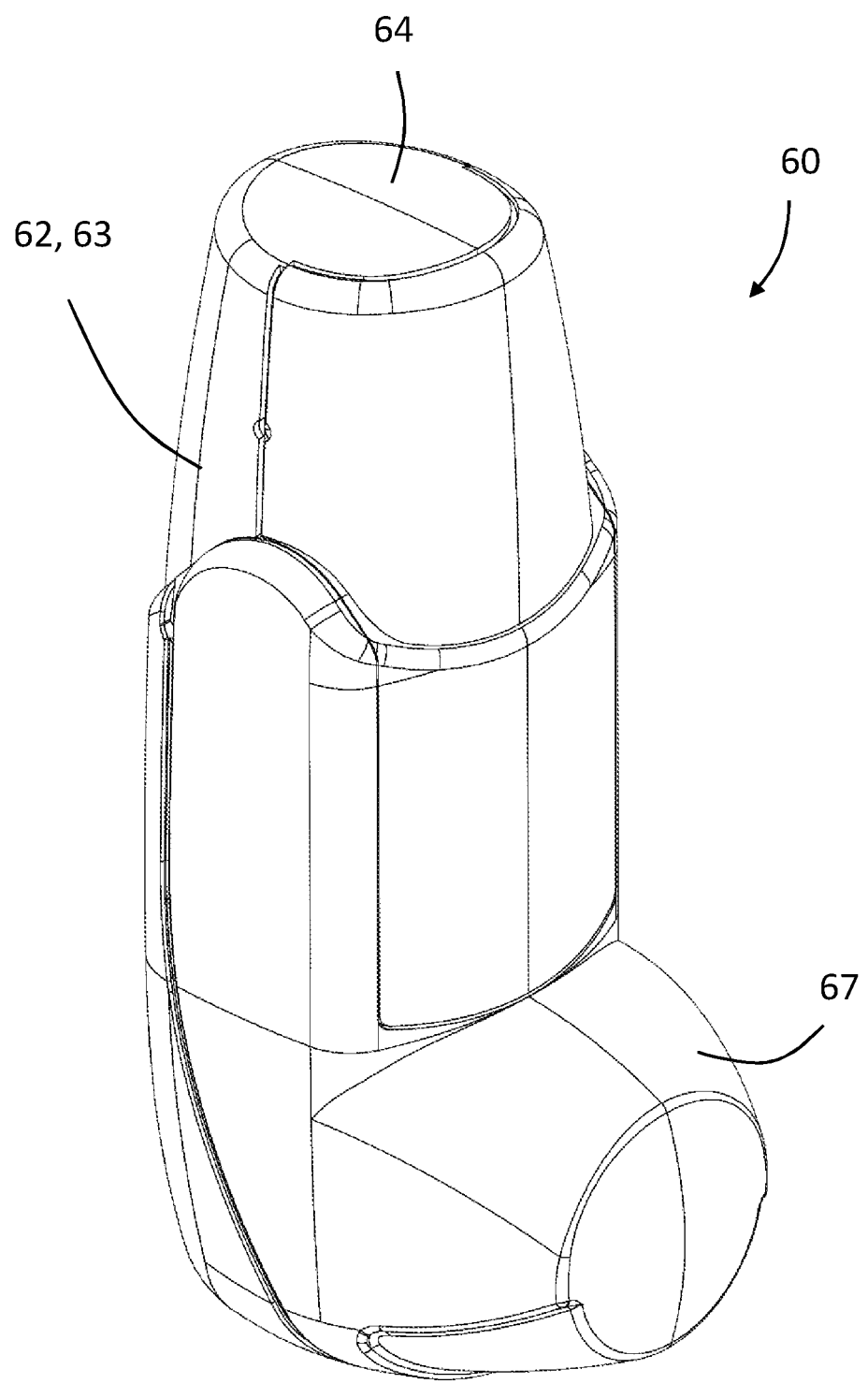
FIG. 2 is a first perspective view of a first pMDI inhaler in accordance with the present invention.
Figure 3:
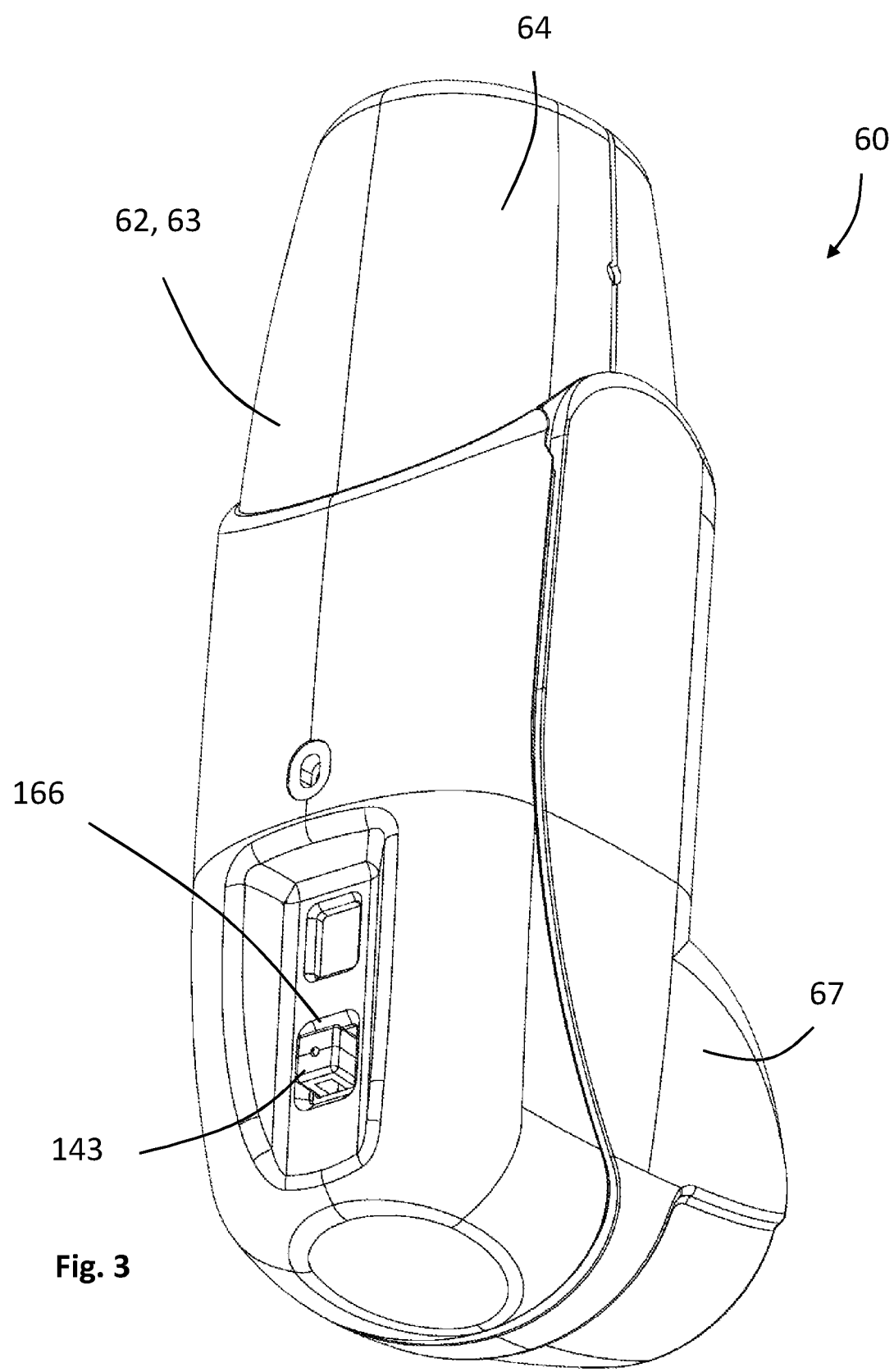
FIG. 3 is a second perspective view of the pMDI inhaler of FIG. 2.
Figure 4:
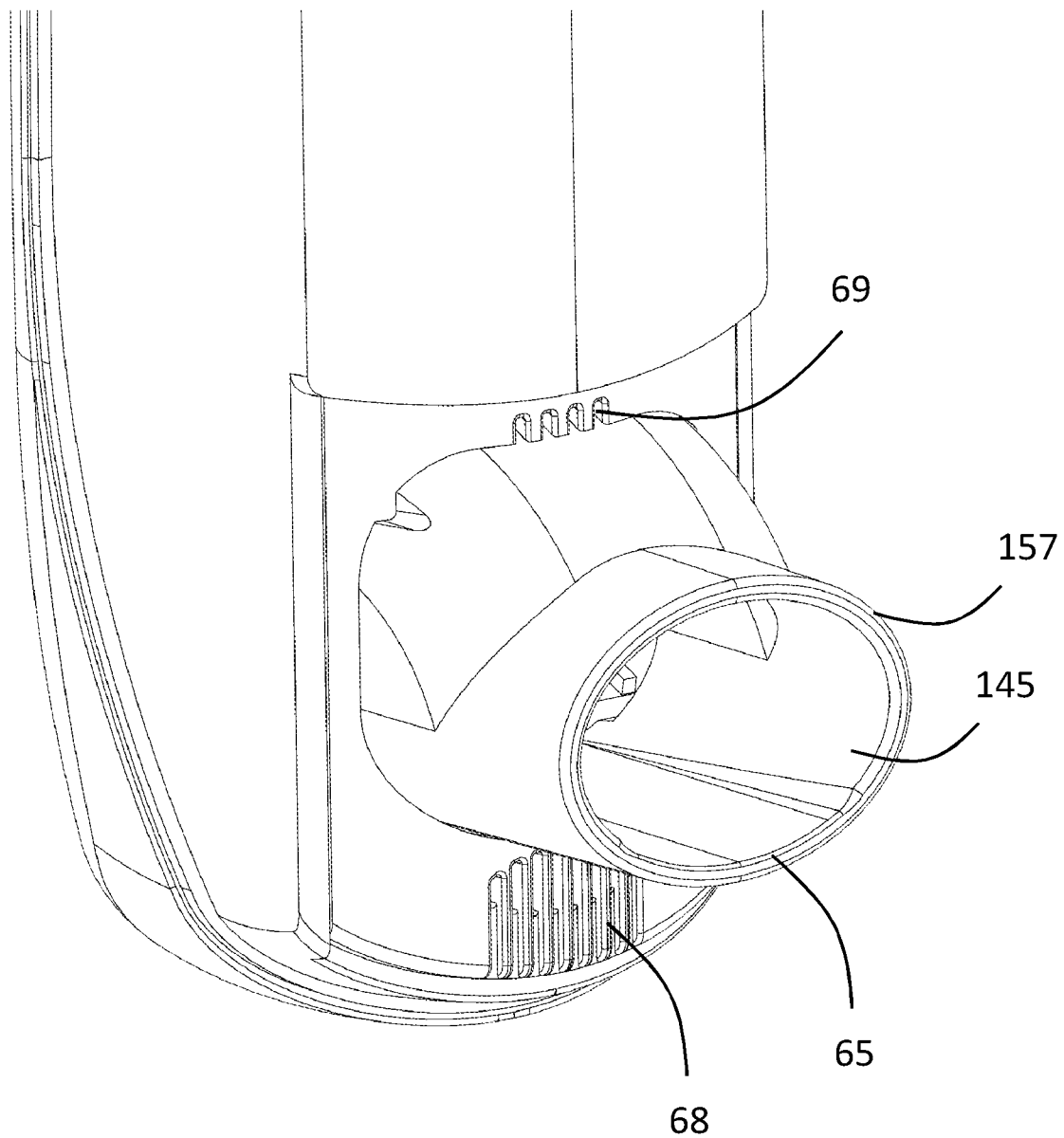
FIG. 4 is a detail perspective view of a part of the pMDI inhaler of FIG. 2.

FIGS. 2 to 4 show perspective views of a first pressurized metered dose inhaler (pMDI) 60 in accordance with the present invention. A housing 62 comprises a main housing body 63. A canister 61 (not shown in FIGS. 1 to 4) sits within the main housing body 63. The canister 61 is identical to the canister 51 of FIG. 1. The main housing body 63 comprises a generally tubular sleeve portion 64 dimensioned to receive and enclose the canister 61 and a portion in the form of a patient port 157 (e.g., in the form of a mouthpiece 65) that defines an inspiration orifice (or an air outlet) 145. Such a patient port of an inhaler is sometimes referred to herein as a "mouthpiece" for simplicity. However, it should be understood that such mouthpieces can instead be configured to be nosepieces of nasal inhalers and that the present disclosure can equally apply to nasal inhalers even where not specifically mentioned herein. The housing further comprises a mouthpiece cover 67 which is rotatably attached to the main housing body for movement between a first position (shown in FIGS. 2 and 3) in which the mouthpiece 65 is covered and a second position (FIG. 4) in which the mouthpiece 65 is uncovered. A first aspiration orifice, or an air inlet, 68 and a second aspiration orifice 69 are defined adjacent the mouthpiece 65. The first aspiration orifice 68 and the second aspiration orifice 69 are also covered, along with the mouthpiece 65, when the mouthpiece cover 67 is in its first position. These features will be described in more detail below.

Figure 5:
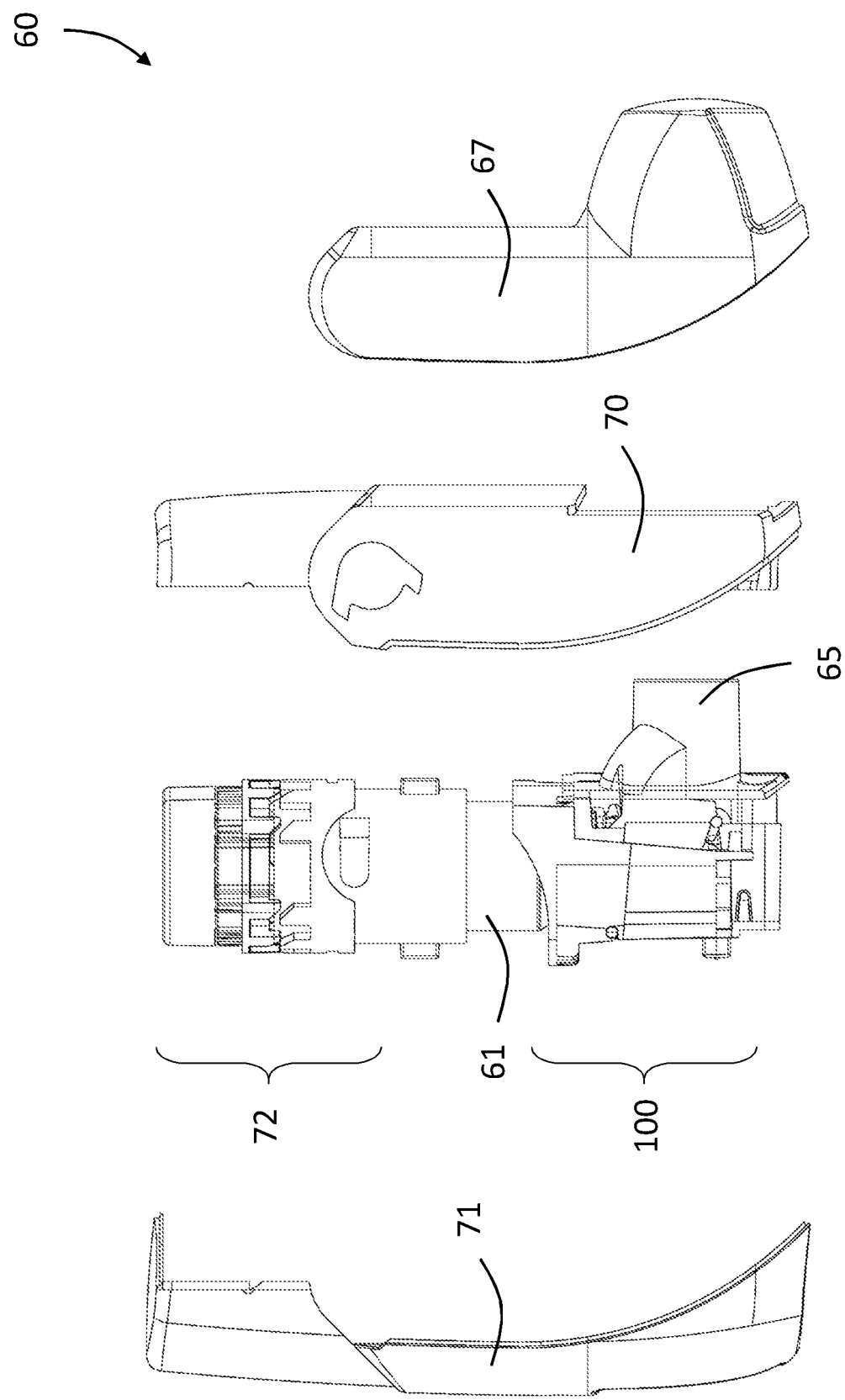
FIG. 5 is an exploded view of the pMDI inhaler of FIG. 2.

FIG. 5 shows a partially exploded view of the pMDI 60. The main housing body 63 comprises a first part 70 and a second part 71. When assembled together, the first and second parts 70, 71 define a volume into which the canister 61 is received. The pMDI 60 comprises a canister actuation mechanism 72 positioned at an end of the housing 62 opposite to the mouthpiece 65, and a breath-actuated trigger mechanism 100 positioned proximate the mouthpiece 65. Both the canister actuation mechanism 72 and the breath-actuated trigger mechanism 100 control the actuation of the canister 61 to automatically dispense the canister contents as will be described below.

Figure 6:
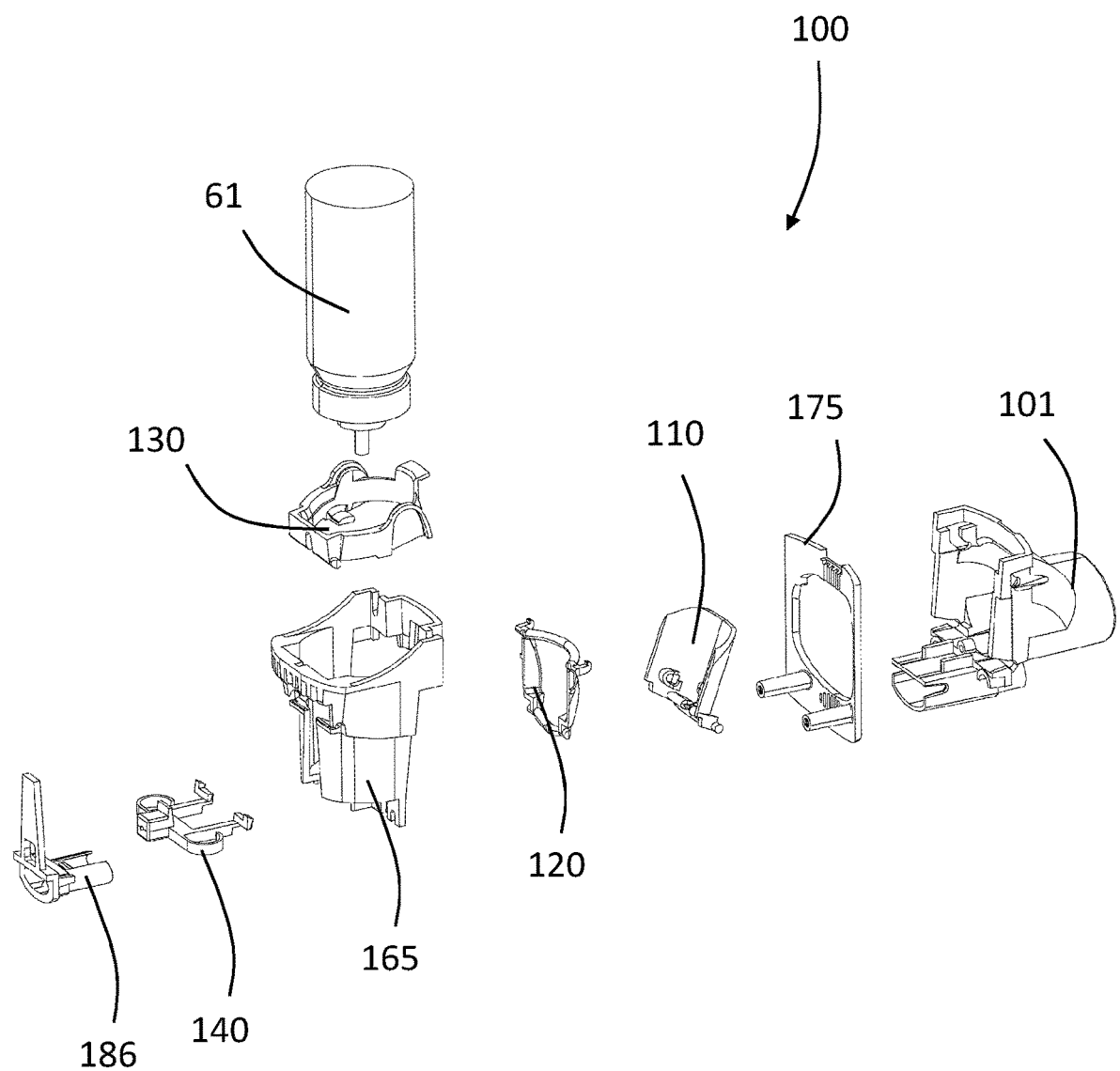
FIG. 6 is a first exploded view of a subassembly of the pMDI inhaler of FIG. 2, shown together with a canister.
Figure 7:
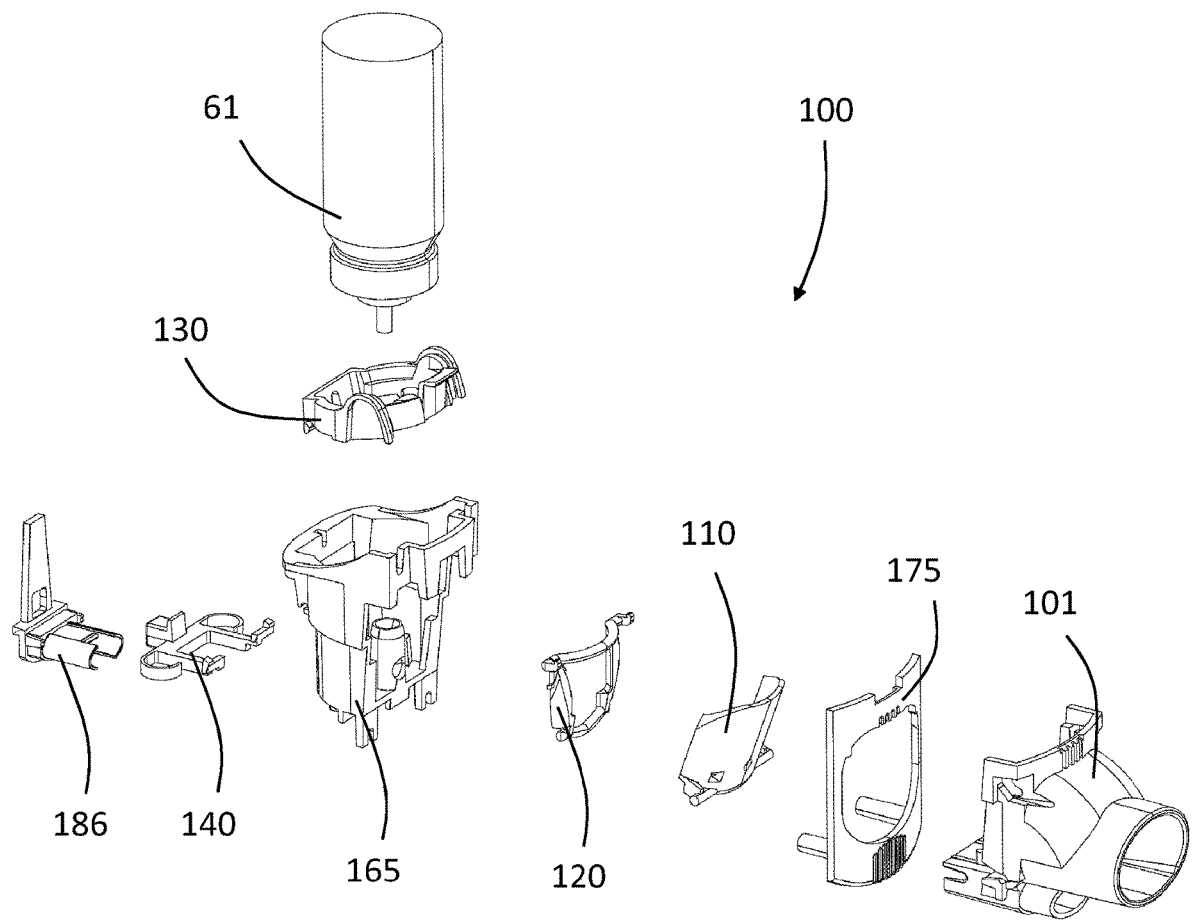
FIG. 7 is a second exploded view of the subassembly of FIG. 6, shown together with part of a canister.

FIGS. 6 and 7 show exploded views of the breath-actuated trigger mechanism 100 of the present invention. The trigger system 100 comprises a lower body component 165, a trigger mechanism chassis 101, a breath responsive member in the form of vane 110, a toggle link 120, an actuation arm 130, a fascia component 175, a flow governor support component 186 and a button component 140. The trigger mechanism 100 is configured to accept the canister 61.

Figure 8:
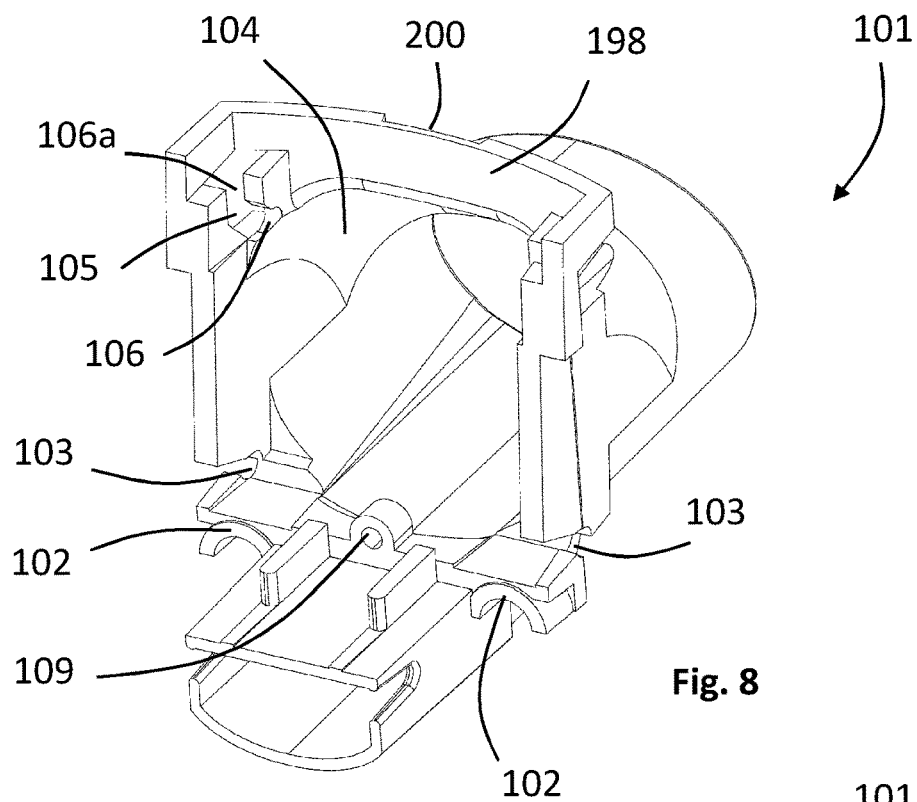
FIG. 8 is a perspective view of a first part of the subassembly of FIG. 6.
Figure 9:
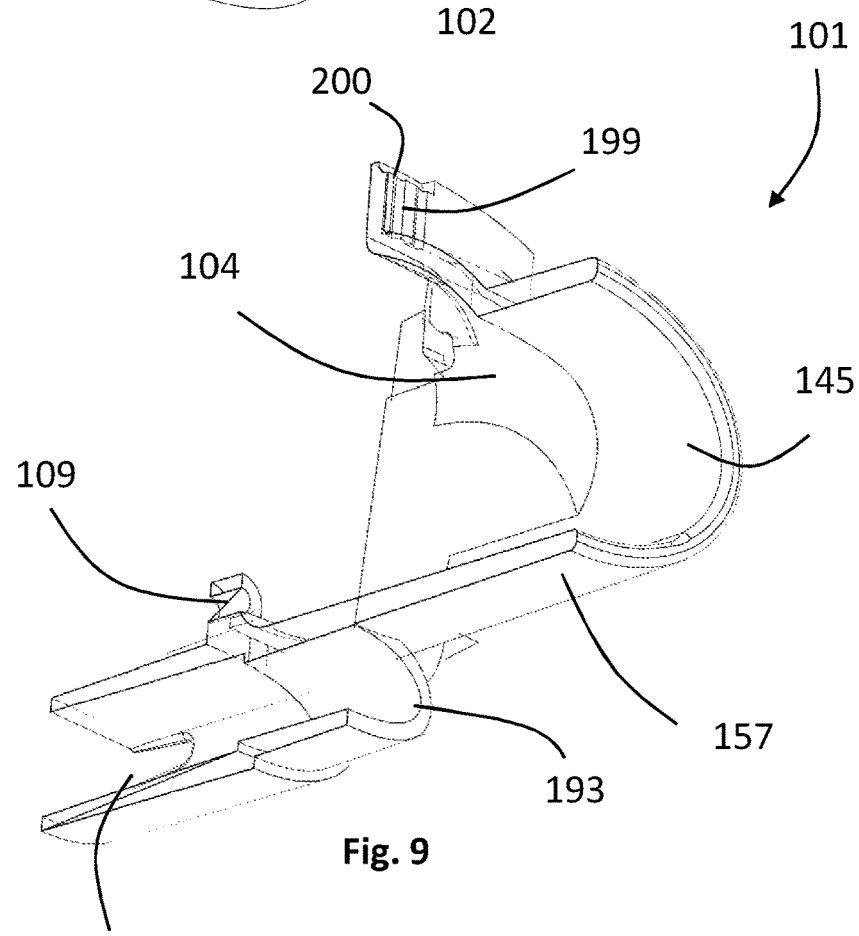
FIG. 9 is a perspective section view of the part of FIG. 8.

FIGS. 8 and 9 show views (FIG. 9 being a section view) of the trigger mechanism chassis 101. The trigger mechanism chassis 101 comprises a hollow tube forming the mouthpiece 157 defining the air flow outlet 145, a wall providing a swept arc 104, toggle axle tracks 105 which define follow-through tracks 106 and primary tracks 106a and axle location features 103. A flow governor passageway 190 is provided adjacent and below the mouthpiece 157 having an inlet opening 193 at the first air inlet 68. The trigger mechanism chassis 101 also provides a sheath 109 to retain the end of a spring, and comprises two semi-tubular location features 102. The trigger mechanism chassis 101 also comprises an upstanding wall 198 projecting radially from the swept arc 104. The wall 198 defines a series of flow passages 199 extending from the arc 104 to the free (upper) end of the wall 198. These flow passages 199 are formed adjacent the second air inlet 69. The flow passages 199 terminate in a first part 200 of a concave valve seat 203 (labelled in FIG. 18). The trigger mechanism chassis 101 is preferably injection moulded from a plastic material.

It will be noted that the first and second inlets 68, 69 face in the same direction as the outlet 145. This means that the inspiration flow must change direction, and further is channelled past the outlet of the canister 61 (as will become apparent below).

Figure 10:
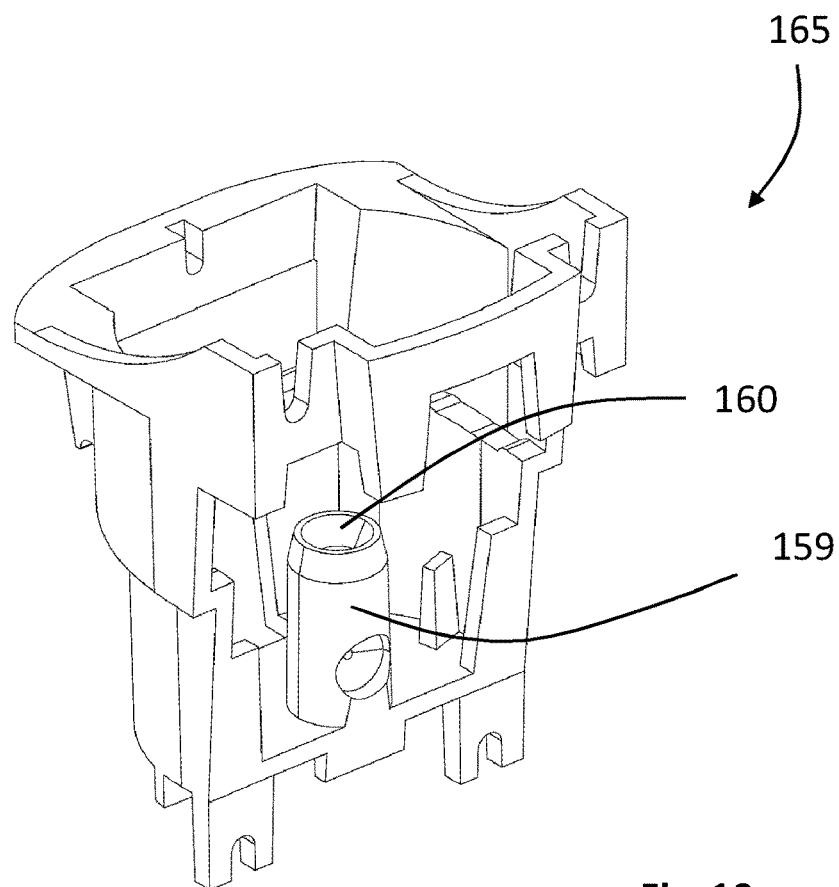
FIGS. 10 and 11 are perspective views of a second part of the subassembly of FIG. 6.
Figure 11:
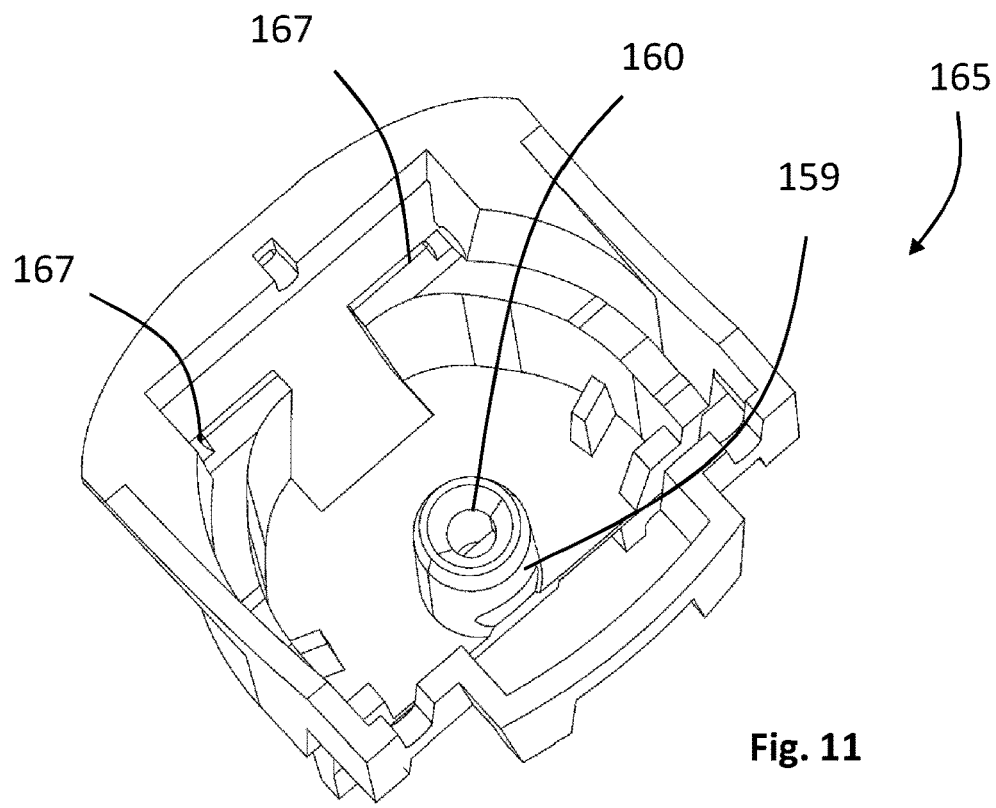

FIGS. 10 and 11 show the lower body component 165, comprising a nozzle block 159 defining a stem socket 160. The lower body component 165 also provides a chassis to support other components of the breath-actuated trigger mechanism. The lower body component 165 includes bearings 167 to receive actuation arm pivots. The lower body component 165 is preferably injection moulded from a plastic material.

Figure 12:
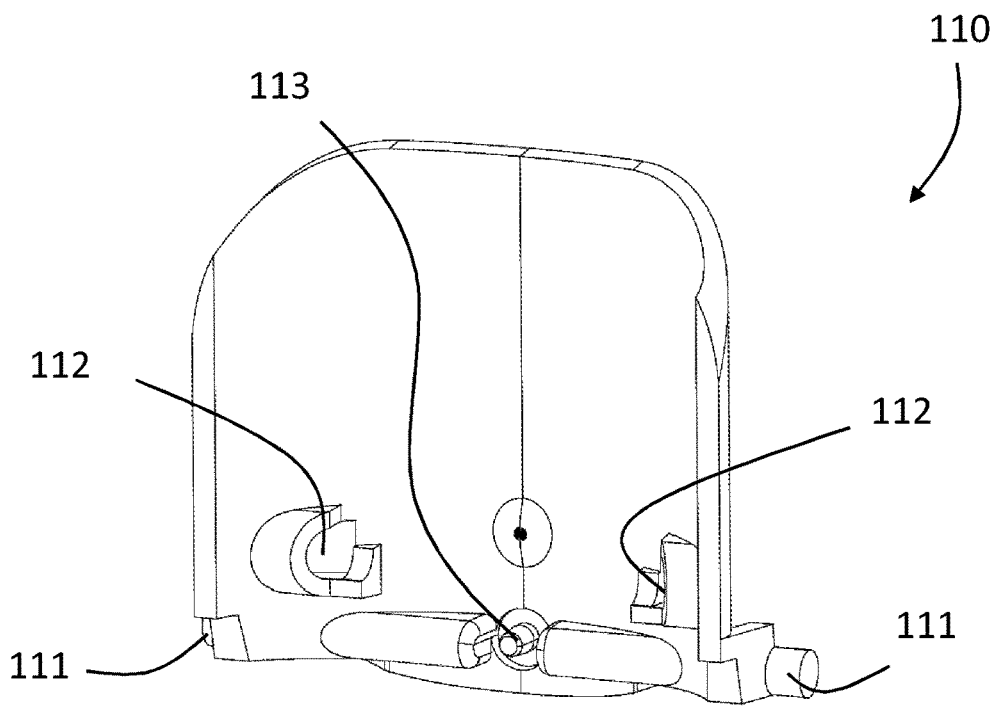

FIG. 12 shows the vane 110. The vane 110 comprises a curved vane wall with a vane pivot in the form of stub axles 111 at one end, and with toggle link pivot location features 112 formed some way along the vane wall from its end with the stub axles 111. The vane 110 also comprises a boss 113. The vane 110 is preferably injection moulded from a plastic material.

Figure 13:
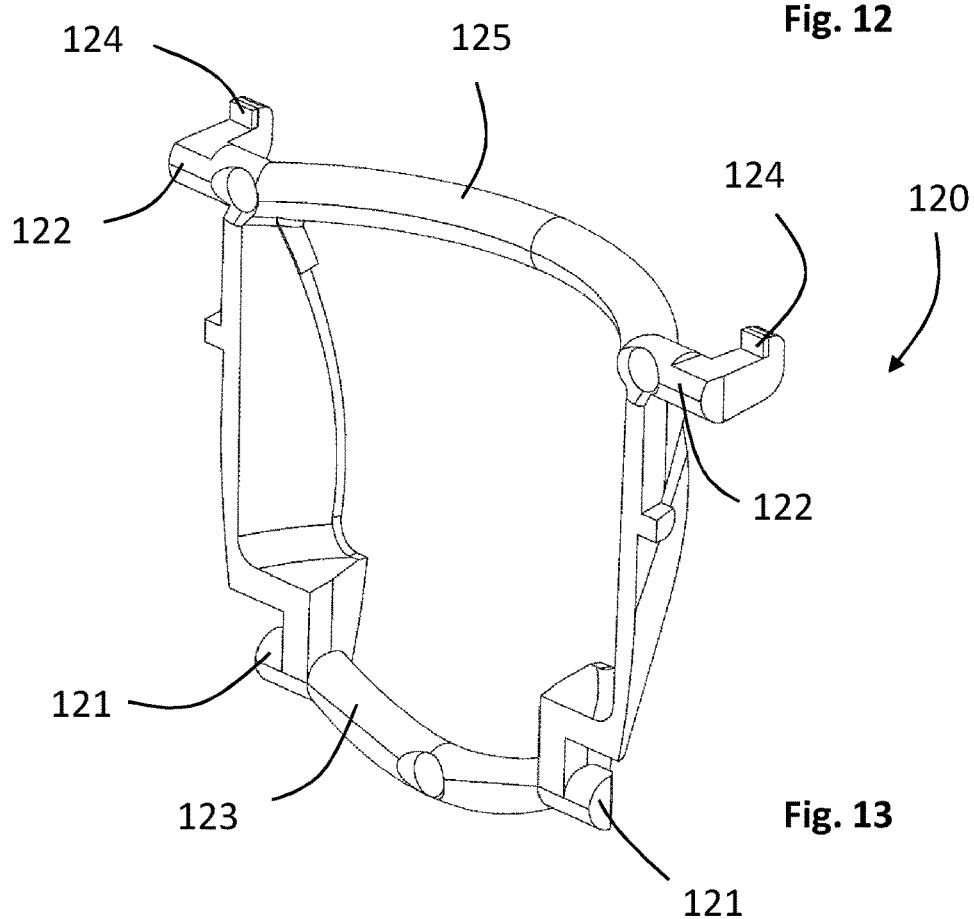

FIG. 13 shows the toggle link 120. The toggle link 120 is in the form of a generally rectangular frame, comprising two side walls linked at the top by an upper bar 125 and linked at the bottom by a lower bar 123. The upper bar 125 is curved forwards and extends outwards at each end beyond the rectangular frame, the outward extensions being in the form of stub axles 122 bearing bosses 124. The lower bar 123 is curved downwards and extends outwards at each end beyond the rectangular frame, the outward extensions being a toggle pivot in the form of stub pivots 121. The toggle link 120 is preferably injection moulded from a plastic material.

FIG. 14 shows the actuation arm 130. The actuation arm 130 is ring-shaped and has a vertical plane of symmetry. The actuation arm 130 bears two stub pivots 133 at a first end. Opposite the first end there is provided a radially outwardly extending tab 201 at a second end. The vertical plane of symmetry intersects the tab 201. A valve member 202 is provided at the free end of the tab 201. Two follow-through bosses 134 are provided between the pivots 133 and the tab 201. Next to each boss 134 is an integral spring arm 132. On the inside edge of the actuation arm, part way between the pivots 133 and the bosses 134 are two ledges 131 (one of the ledges being concealed in FIG. 14 by a wall of the actuation arm). The actuation arm 130 is preferably injection moulded from a plastic material. To confer appropriate properties for the spring arms 132, the plastic material is preferably an acetal material.

FIG. 15 shows the fascia component 175. The fascia 175 comprises a generally flat plate comprising an aperture 176 to receive the mouthpiece 157. At its lower end, the fascia 175 comprises two location features 177 that can engage with the tubular location features 102 on the trigger mechanism chassis 101. The fascia 175 also forms a first grill 194 between the location features 177. The first grill 194 defines a series of apertures 207. A second grill 195 is provided on the opposite side of the aperture 176 to the first grill 194. FIG. 15a shows the second grill 195 in more detail (FIG. 15a being a detail view of area "a" in FIG. 15). The second grill 195 defines a plurality of flow passages 204 extending from a plurality of inlet channels 205 to the free (upper) end of the fascia component 175. The flow passages terminate in a second part 206 of the concave valve seat 203 (labelled in FIG. 18). The first grill 194 provides the entry point for the first fluid inlet 68, and the second grill 195 provides the entry point for the second fluid inlet 69. The fascia component 175 is preferably injection moulded from a plastic material.

Figure 16:
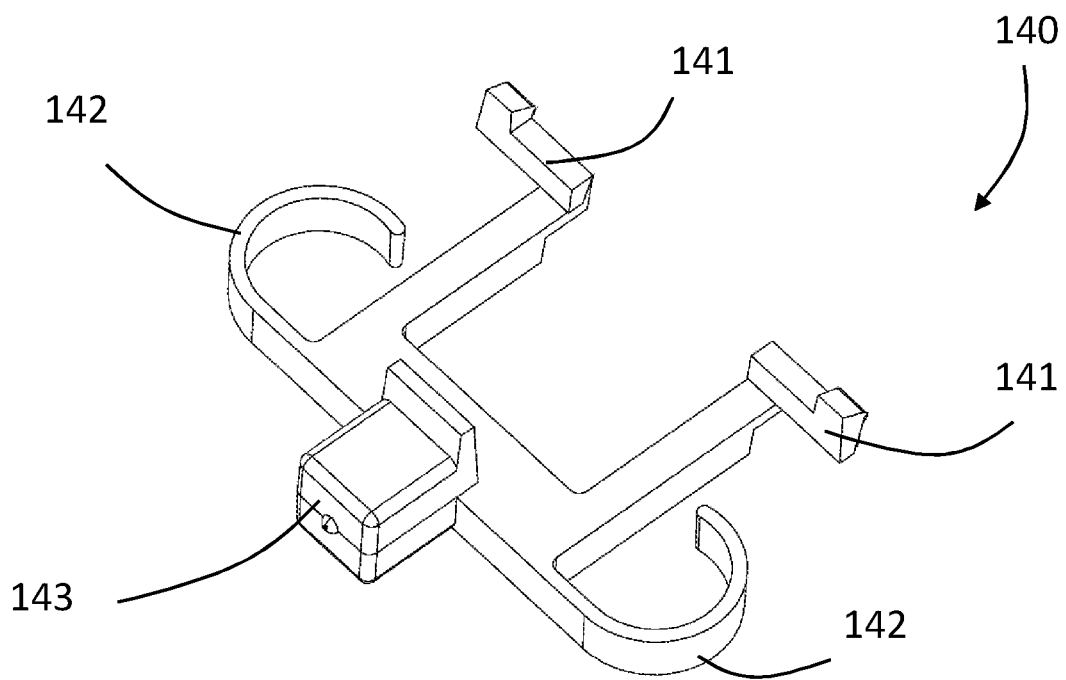

FIG. 16 shows the button component 140. The button component 140 comprises a protruding button 143 at one end, and two contact features 141 at the other end. The button component 140 also comprises two integral return spring arms 142. The button component 140 is preferably injection moulded from a plastic material. To confer appropriate properties to the spring arms 142, the plastic material is preferably an acetal material. The button component of FIG. 16 serves as an override feature that allows the patient to use the inhaler in a press-and-breathe mode, and may be used to prime the metering valve if required. In embodiments in which it is present, the override enables the patient to use it to press forward against the back of the toggle mechanism 119 (which will be described below) (e.g., against the back of the vane) to move the vane to an angle past its trigger point. When the valve is then actuated, the toggle mechanism 119 will already be in an unlocked position but will still be forced into the actuated position (with the vane against the floor of the mouthpiece). In other words, with the override button pressed the device will act similarly to a conventional press-and-breathe inhaler.

Figure 17:
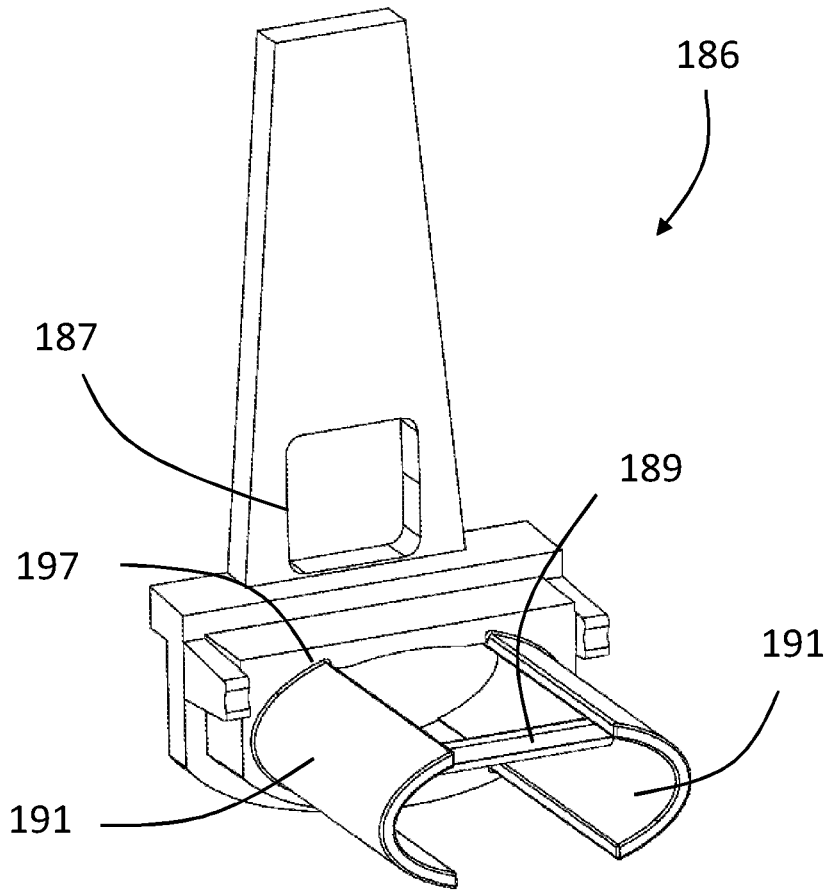

FIG. 17 shows the flow governor support component 186. The flow governor support component 186 comprises a base 197 on which a collapsible silicone tube flow governor component (described below) can be mounted. The internal support structure of the flow governor is provided by two curved, part-elliptical support features 191 formed on the flow governor support component 186. The support features 191 are joined by a cross-member or cross-beam 189. Additionally, the flow governor support feature extends upwards at its back into a wall with an aperture 187 in it. When the flow governor support component 186 is assembled onto the lower body component 165, this aperture 187 provides a location for the button 143 to protrude for access by the patient.

FIG. 21a shows a flow governor component 310. The flow governor component 310 is a flexible tubular element constructed (in this embodiment) from a silicone material. The flow governor component 310 has a substantially uniform cross-sectional shape, which here is approximately an ellipse, e.g., a circle.

Assembly

FIGS. 18 to 20a show a breath-actuated trigger mechanism 100 assembled from the components shown in FIGS. 6 to 17, shown in its rest (unactuated) position. The trigger mechanism chassis 101 is attached to the lower body component 165, and the fascia 175 sits over the trigger mechanism chassis 101. The fascia component 175 and the trigger mechanism chassis cooperate such that the flow passages 199 and flow passages 204 cooperate to form flow paths from the apertures 205 (at the second fluid inlet 69) to the valve seat 203. The apertures 207 of the first grill 194 allow air flow from the first fluid inlet 68 into the flow governor passageway 190.

The collapsible silicone tube flow governor component 310 (similar to that disclosed in PCT Publication WO 2017/112748) is mounted on the flow governor support component 186. The support features are received within the lumen of the flow governor component 310. As shown in FIGS. 21b and 21c, the component 310 is supported in a fully open condition by the support features 191, which are held in position by the cross-beam 189. The flow governor support component thereby defines a central lumen through which air may flow under the influence of a patient-imposed inspiratory pressure drop as will be discussed below.

The outer diameter of the base 197 is greater than an initial inner diameter of the flow governor component 310, and assembly of the two components can be achieved by stretching the flow governor component 310 over the base 197. This positioning results in the original (e.g., circular) cross-section of the tubular element 102 being deformed into an approximately elliptical (e.g., approximately elliptical with a greater aspect ratio than before) cross-sectional (i.e., in transverse cross-section) shape.

Figure 19:
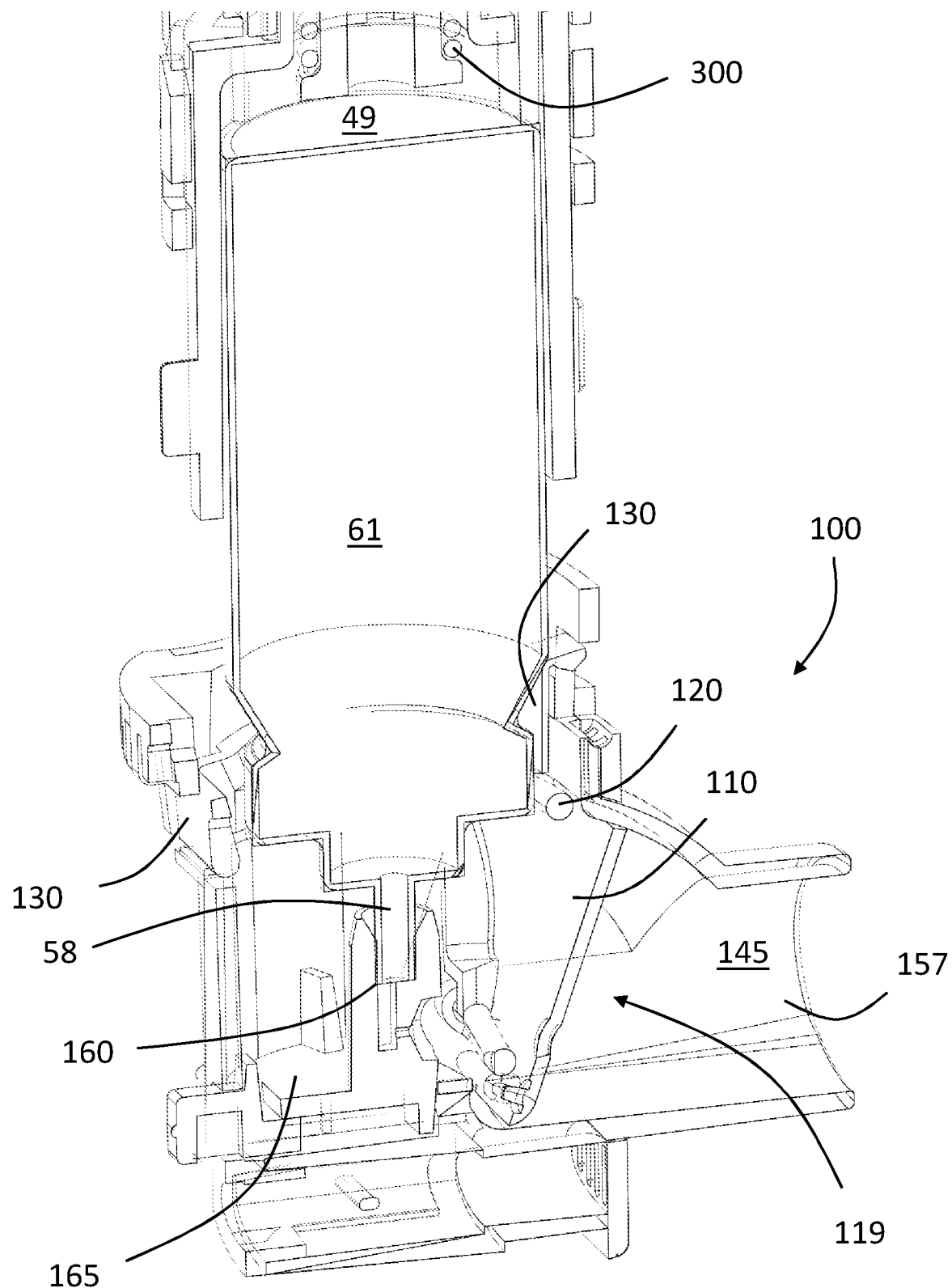
FIG. 19 is a perspective section view of the subassembly of FIG. 6 in an unactuated, rest condition, shown together with a canister and part of a canister loading mechanism for loading the canister.
Figure 20A:
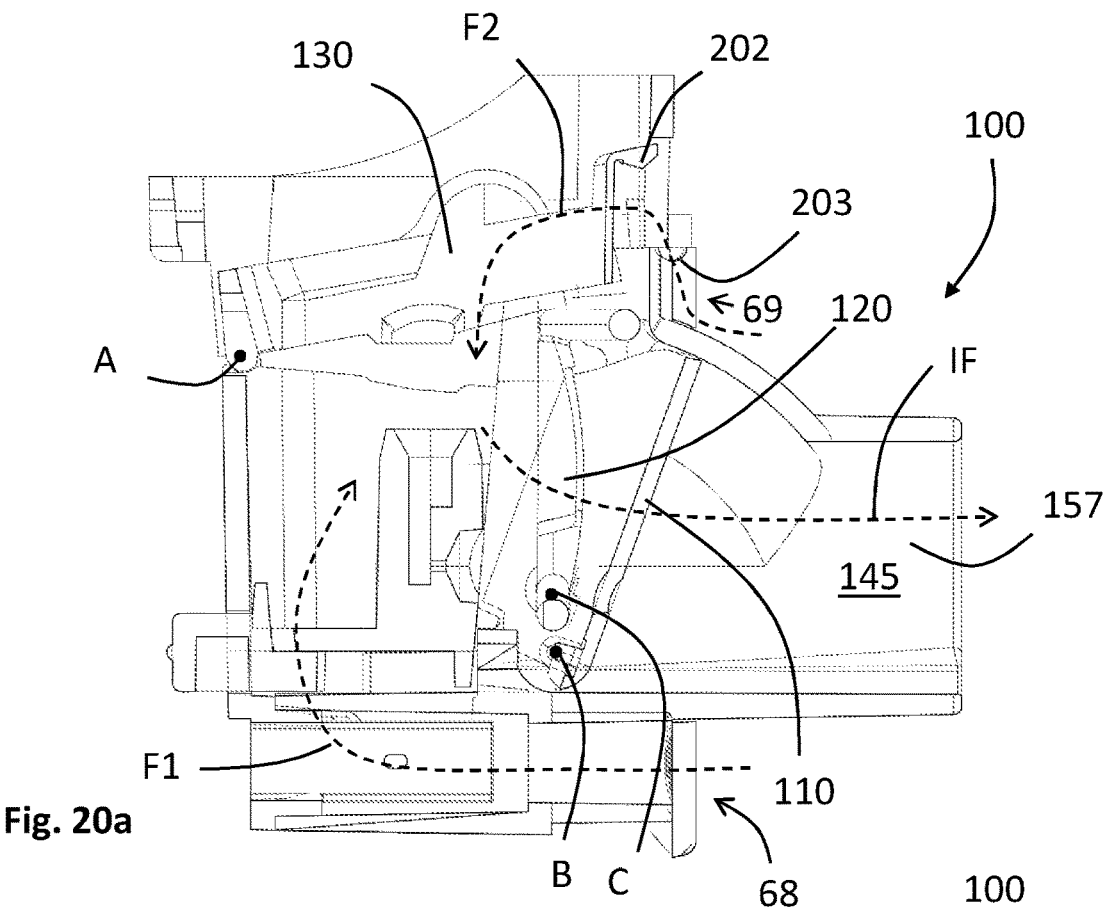
FIG. 20a is a section view of the subassembly of FIG. 6 in an unactuated, rest condition.
Figure 20B:
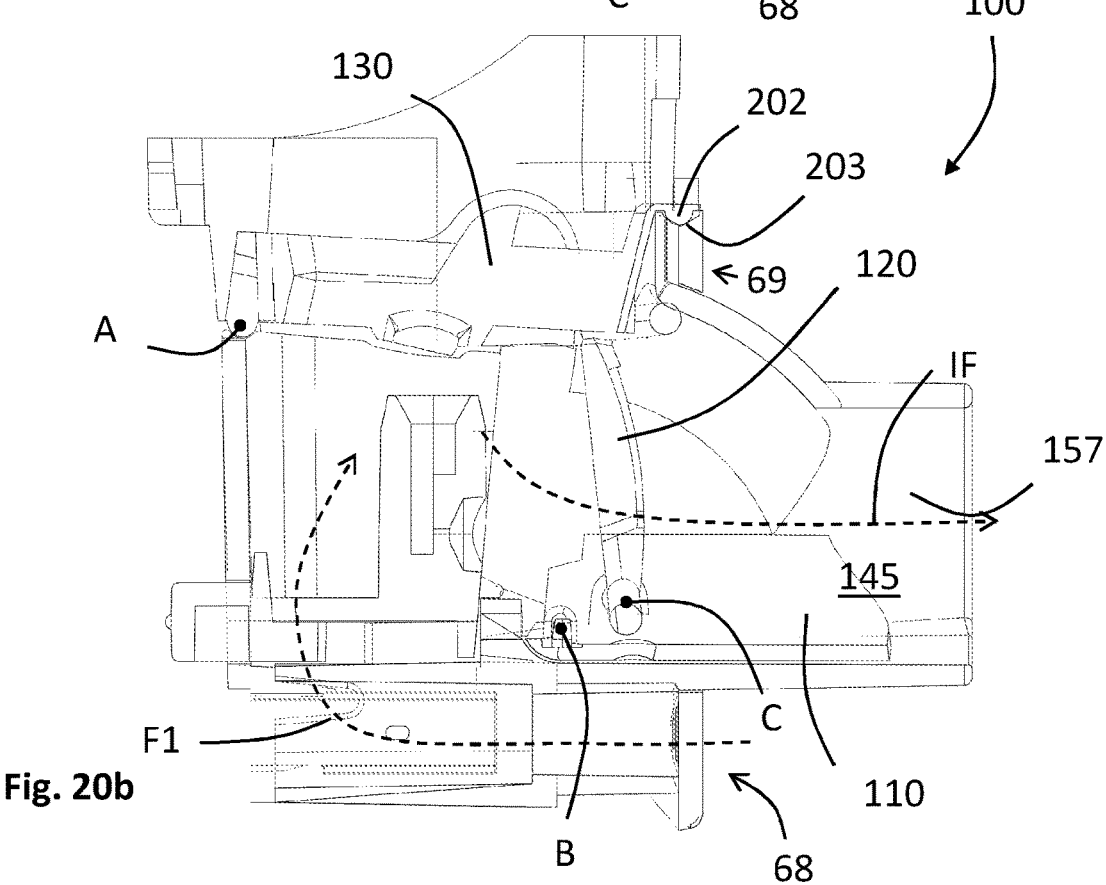
FIG. 20b is a section view of the subassembly of FIG. 6 in an actuated condition.
Figure 22:
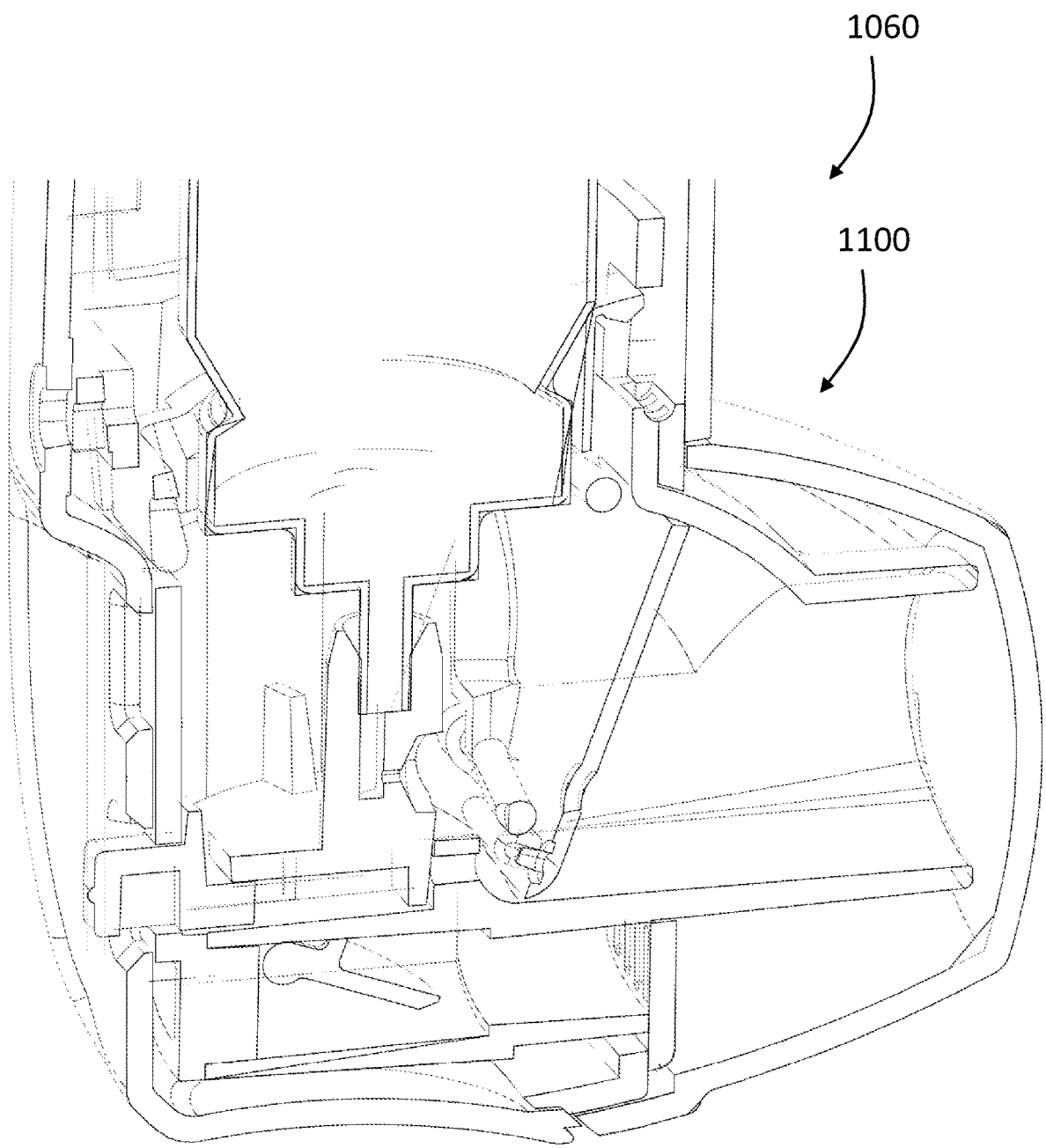
FIG. 22 is a perspective section view of a part of a second pMDI inhaler in accordance with the present invention.

As shown in FIGS. 19, 20*a* and 20*b*, the actuation arm 130 is mounted in the lower body component 165, the stub pivots 133 of the former being rotatably mounted in the bearings 167 of the latter for rotation about axis A. The front of the actuation arm 130 rests on the upper end of the toggle link 120 when the mechanism is at rest (FIG. 20*a*), with the spring arms 132 also contacting the toggle link 120.

The vane 110 is mounted within the trigger mechanism chassis 101, with the vane's stub axles 111 engaged in the location features 103 of the trigger mechanism chassis 101 and with the vane's curved wall within the swept arc 104 of the trigger mechanism chassis 101. The vane can rotate relative to the chassis 101 about axis B (FIG. 20*a*).

The toggle link 120 is also mounted within the trigger mechanism chassis 101, with its stub axles 122 in the toggle axle tracks 105 when the toggle link 120 is in its rest position. The vane 110 and toggle link 120 form the toggle mechanism 119 as will be described in further detail shortly. The stub pivots 121 at the bottom of the toggle link 120 are engaged with the toggle link pivot location features 112 on the back of the vane 110, the engagement being in the form of a rotatable hinge about an axis C (FIG. 20*a*).

Figure 18:
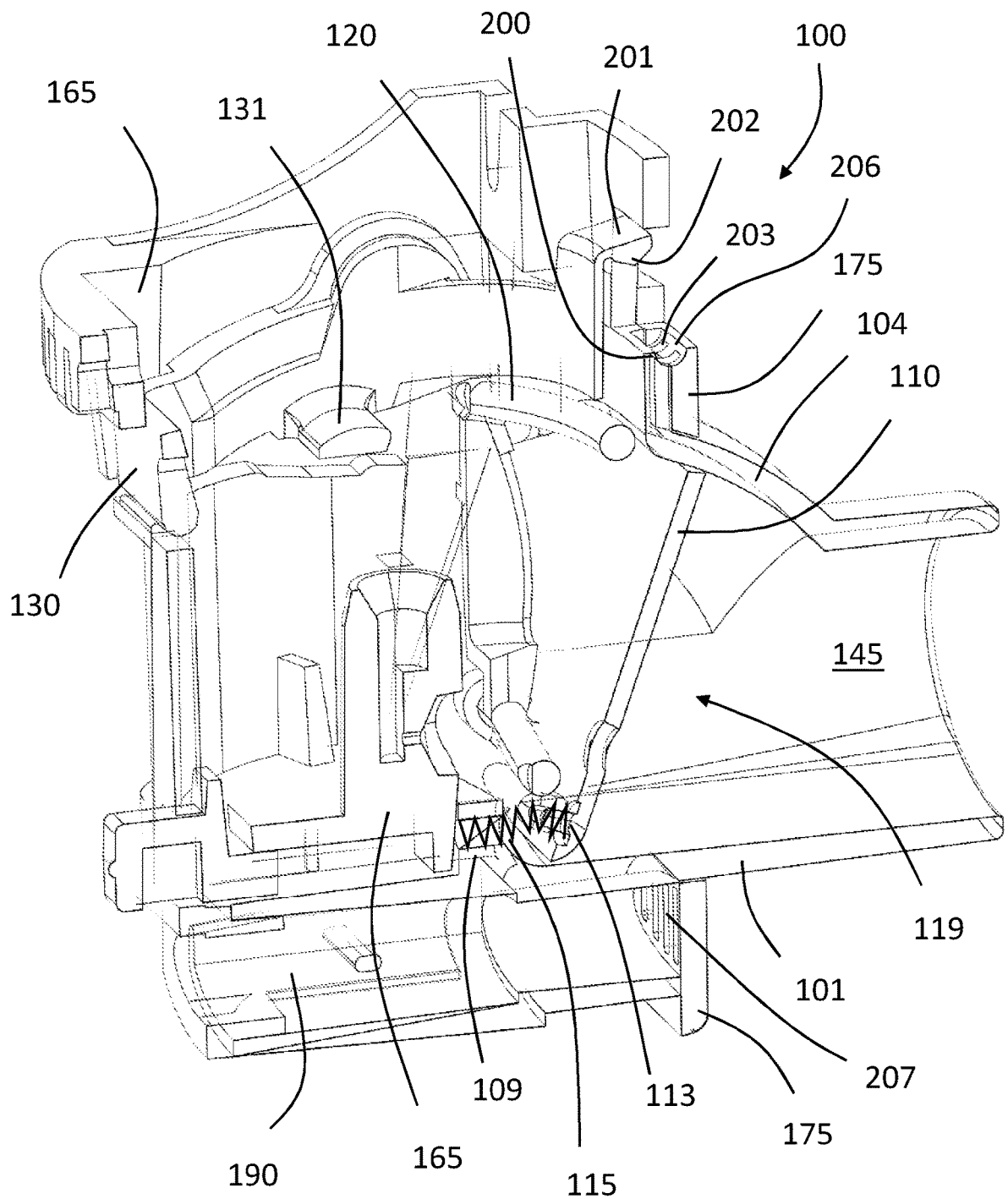
FIG. 18 is a perspective section view of the subassembly of FIG. 6 in an unactuated, rest condition.

A spring 115 is provided (shown in FIG. 18 only), being a helical spring having a longitudinal axis of flexure. That is to say, the spring 115 has a centre line that runs along the centre of the helix from one end of the spring 115 to the other. That centreline (which need not be a straight line within the scope of the invention) defines the longitudinal axis along which the spring flexes. During flexing the shape of that longitudinal axis bends as the spring is loaded or unloaded. The primary reactionary force offered by the spring 115 results from longitudinal flexure rather than compression or extension of the spring along the line of the longitudinal axis. The spring 115 is mounted at a first end to the inside of the sheath 109 of the trigger mechanism chassis 101 and at a second end over the boss 113 on the vane 110. When the breath-actuated trigger mechanism of FIG. 18 is at rest, the spring 115 is slightly bent upwards in the centre by virtue of a deliberate misalignment between the boss 113 and the sheath 109. This bend provides a small residual spring force when the mechanism is at rest, thereby holding the vane 110 in the rest position, this force increasing the stability of the at-rest (e.g., primed, ready to trigger) mechanism slightly.

Operation

In use, a conventional pMDI canister 61 (shown in FIG. 19) is placed into the mechanism 100, with the tip of its stem 58 engaging with the stem socket 159, and with the underside of its metering valve contacting the two ledges 131 on the actuation arm 130.

In use, a force is applied to the canister 61. This may be direct (by a user's hand) or by means of energy stored in a spring or other resilient means. The actuation arm 130 is used to transmit the force, from the pMDI canister, to the trigger mechanism 100. However, resistance from the trigger mechanism 100 via the actuation arm 130 prevents the canister 61 from moving, and hence prevents the metering valve 54 from firing, until the toggle mechanism 119 is actuated. The actuation arm 130 contacts the ferrule of the pMDI canister approximately half way along its length and engages the toggle link 120 at its other end. This configuration results in reduction in the force that is applied to the toggle mechanism 119, giving an approximate additional mechanical advantage of 2:1. In other words, the toggle mechanism 119 can resist a force from the canister of approximately twice its own resistive force. The actuation arm also has the spring arms 132 attached to it which act against the toggle link 120 and provide sufficient force to return the actuation arm 130 after actuation.

At rest, as shown in FIGS. 19 and 20*a*, the mechanism 100 is stable, with the toggle link 120 supporting the load that the patient applies to the canister's base 49 via a deformed (e.g., compressed) resilient member 300.

There are two fluid inlets 68, 69 through which air can enter the inhaler.

A first fluid flow path is shown as F1 in FIG. 20*a*, and a second as F2. Only the air outlet end of the flow governor component 310 is fixed and supported (i.e. by the base 197), whereas the air inlet end of the flow governor component 310 is freestanding and able to collapse onto the internal support structure.

The primary function of the flow governor is to govern air flow when the patient inhales through the inhaler, limiting the patient's inspiratory flow rate to a narrow and controlled range in order to avoid excessively fast inhalation and consequently excessive mouth and throat drug deposition. The flow governor of the present disclosure is thus able to aid in the attainment of increased deep lung drug penetration and deposition. Use of such a flow governor allows patients with poor lung function (e.g., particularly poorly COPD patients) to experience a relatively low inhaler air flow resistance (allowing them to inhale sufficient air in a reasonable degree of comfort) while giving patients with stronger lungs a transiently higher air flow resistance to inhale against (thereby allowing them to inhale for longer and more deeply, while at the same time limiting their inhalation air flow rate to a level very similar to that of weaker patients). In other words, the inspiratory air flow rate can be kept much more consistent between patients and between inhalations. Medication delivery is thus much more predictable, allowing physicians to prescribe treatment regimes with an improved level of confidence.

FIG. 21*b* illustrates the flow governor at rest (i.e., with the flow governor component 310 in an uncollapsed state). FIG. 21*c* shows the flow governor in an operative state (i.e., with the patient's inspiratory air flow substantially passing through it and with the flow governor component 310 in a collapsed state).

When air is sucked along the flow path F1 (FIG. 20*b*) it flows into the flow governor component 310, between the support features 191 and past the cross-member 189. The speed of the passing air flow through the air flow path creates a reduction in air pressure in the air flow path F1 (i.e. according to the Bernoulli Effect). The reduced pressure in the air flow path F1 causes a reduction in the diameter along the minor axis of the elliptical cross-sectioned flow governor component 310 (i.e., in the transverse direction T) resulting in inward bending, as shown in FIG. 21*c*. Because the flow governor component 310 is supported at one end (i.e. its outlet end) by the base 197, the inward bending occurs predominantly at the end of the flow governor component 310 that is towards the air inlet 68, the inward bending restricting the cross-sectional area of the air flow path.

To an extent, the greater the reduction in pressure in the air flow path F1, the greater the inward bending of the flow governor component 310. The resultant reduction in the cross-sectional area of the air flow path leads to an increased resistance to air flow rate. However, because the air flow path of the flow governor is only one part of the total overall resistance to air flow of the medicinal inhaler in which the flow governor is employed (e.g. it might be around 50% or less of the total inhaler air flow resistance if the inhaler has a moderate static resistance to air flow), then the mass flow rate of air through the flow governor does not fall in proportion to its reduced residual cross-sectional area. This means that the velocity of air through the residual air flow path within the flow governor component 310 rises as the flow governor component 310 collapses, further increasing the Bernoulli forces upon it. This effect tends to lead to substantial bistability in the operation of the flow governor. That is, the initiation of collapse leads to "positive feedback" which reinforces the inwards collapse-driving Bernoulli forces until they are eventually balanced by the resistive stiffness forces of the material of the flow governor component 310. In other words, in some embodiments, the flow governor 101 can be substantially bistable, where it tends to be in one of two states at any time: either it is in a substantially 'open' or 'uncollapsed' state (FIG. 21b), or it is in a substantially 'collapsed' state (FIG. 21c).

Complete collapse of the elliptical cross-section tubular element 102 is prevented by the support features 191. These features, together with the cross-member 189, provide structural support that prevents significant reduction in the diameter along the major axis of the flow governor component 310 (i.e., in the lateral direction L).

The finite stiffness of the flow governor component 310 means that small additional gaps are left around the corners of the internal support structure formed by the features 191 and cross-member 189 where the flow governor component 310 cannot bend sufficiently to close off all the small residual air passageways or gaps between the internal support structure and flow governor component 310 (see FIG. 21c). Thus, at least a minimum, or residual, air flow can always continue to flow. That is, the reduced pressure can never reach a value sufficient for the flow governor component 310 to collapse completely and to seal off all air flow through the flow governor.

The flow governor is reactive to the flow rate of fluid through the first flow path F1, and starts to narrow the lumen through the flow governor passageway as the flow rate increases (via the Venturi effect). Therefore, flow through the first fluid inlet 68 is governed.

The flow through the second inlet 69 at the start of the second flow path F2 passes through the channels formed by the flow passages 199 and the flow passages 204 and enters the inhaler at the valve seat 203 which is fully open, as shown in FIG. 18, when the trigger mechanism 100 is in its rest (unactuated) position. This second flow path F2 is not governed. Both flow paths converge and contribute to an inhalation flow IF.

Because of the ungoverned flow path F2 entering the second fluid inlet 69, the user is free to inhale at a high flow rate (pre-triggering). As the patient inhales, air passes inwardly as described above, along the second flow path F2 and outwardly through the air outlet 145, causing a pressure drop across the two sides (convex and concave) of the curved wall of the vane 110. The flow path F1 also contributes to this inhalation flow IF, but is governed. The pressure drop caused by the inhalation flow IF causes the vane 110 to rotate about axis B, clockwise as drawn in FIGS. 20a/20b, with its stub axles 111 rotating in the location features 103 of the trigger mechanism chassis 101.

The actuated condition of the trigger mechanism 100 is shown in FIG. 20b, as compared to the unactuated condition of FIGS. 19 and 20a. In its actuated position, the vane 110 sits against the base of the mouthpiece. In some embodiments, the vane has been given a specific profile that allows it to sit against the floor of a conventional mouthpiece when actuated, yet to provide sufficient resistance to the airflow whilst in the rest position.

As the vane 110 rotates, the toggle link pivot location features 112 on the back of the vane 110 are displaced towards the open end of the mouthpiece 157. This displacement pulls the stub pivots 121 of the toggle link 120 forwards (i.e. towards the mouthpiece 157), thus unlatching the toggle linkage and overcoming the small restoring force from the bent spring 115 (shown in FIG. 18). With a pre-load applied to the canister base 49, and thence through the canister 51 and its metering valve 54 onto the actuation arm 130 and onto the toggle link 120, the toggle linkage collapses, with the toggle link 120 moving generally downwards (compare FIGS. 20a and 20b). The movement of the toggle link 120 is steered by its bottom stub pivots 121 being pulled round about axis C by the rotational displacement of the toggle link pivot location features 112, and by its top stub axles 122 following the toggle axle tracks 105.

As the canister continues to move downwards under the applied load, the actuation arm 130 in turn pushes the toggle link 120 down until its stub axles 122 leave the primary tracks 106a of the toggle axle tracks 105 and pass into their curved lower portions, i.e., into the follow-through tracks 106. The forwardly curved nature of these causes the stub axles 122 (and thence the top end of the toggle link 120) to move forward, out of the way of the actuation arm 130. This allows the actuation arm 130 to move downwards far enough to allow movement of the canister 51 as far as the total travel of the valve stem 58 into the metering valve 54.

Eventually, the actuation arm 130 will rotate about axis A to a point (shown in FIG. 20b) where the valve convex member 202 engages the concave valve seat 203 and prevents further significant ingress of air through the second fluid inlet 69. In other words, the flow path F2 is blocked. At this point, and as the medicament is released from the canister 61, the majority (if not all) of the airflow into the inhaler is through flow path F1: i.e., it is governed.

The provision of an open (ungoverned) flow path initially allows the user to produce a significant pressure drop across the vane. This pressure drop is higher than that which would be possible with flow only through the governed first inlet 68. As mentioned above, a significant ungoverned flow portion is generally undesirable for medicament inhalation, and as such as the canister 61 releases the medicament, the governed proportion of the inhalation flow is significantly increased (to 100% in some embodiments). This provides a high degree of reliability of actuation coupled with a highly or fully governed flow once triggering has taken place.

In terms of the mechanism itself, it will be noted that even in cases of extreme component dimensional tolerances, the valve stem 58 is allowed to move far enough to release a dose of aerosolised medicament formulation. In other words, the breath-actuated trigger mechanism 100 allows "follow-through" of valve motion after its triggering point. Note that the two follow-through bosses 134 obstruct the upper stub axles 122 and thus hold the toggle link 120 down, thereby preventing the toggle link 120 and the vane 110 from being reset by the vane return spring 115 until the load has been removed from the ledges 131 (e.g., when the load has been released from the canister). The two follow-through bosses 134 also serve to ensure that the toggle cannot ride over the top of the actuation arm 130 and thence wedge it down.

The housing components 70, 71 provide an outer shell into which the breath-actuated trigger mechanism fits. They provide a more attractive and ergonomic form for the patient, and provide protection for the mechanism inside. At the rear of the component 71 there is provided (FIG. 3) a window opening 166 through which the button 143 on the button component 140 can protrude. This button 143 serves as a manual override: if a patient for any reason wishes to take a dose manually, rather than in breath-actuated fashion, then pressing on the button 143 causes the contact features 141 to push against the back of the vane 110, causing the vane to start to rotate as if breath actuated.

Reset of the mechanism occurs as follows. The first step is that the load is removed from the base 49 of the pMDI canister 51, for example either by the patient unloading a firing spring (not shown) in a fully-automated breath-actuated inhaler or by the patient ceasing to press downwards on the base 49 of the pMDI canister 51. Removing the load from the pMDI canister allows the return spring in the valve 54 to reset the valve and allows the spring arms 132 to return the actuation arm 130 to its rest position. As the follow-through bosses 134 move back upwards with the actuation arm 130, the upper stub axles 122 are able to move back up their tracks 106, 106a as the vane spring 115 resets the toggle link 120 and the vane 110. The toggle linkage is thus reset, and the valve seat 203 is again exposed.

To ensure that the spring will return the mechanism reliably, a bending pre-load force is imposed on it. A pre-load ensures that the mechanism will reset even at worst case component dimensional tolerances or if the device friction were to increase slightly due to wear or the presence of drug, dirt or moisture. Using a conventional helical compression spring in this side-loaded configuration—or, alternatively, a helical tension spring (not shown)—provides a low and relatively constant force that can be used to reset the mechanical pMDI breath-actuated trigger mechanism.

The toggle mechanism 119 is designed not to go over-centre, but instead to be held by the friction generated in its stub axles 111 and stub pivots 121. It is also designed to hold back a significant load until the toggle mechanism 119 is moved in a direction that pulls the vane 110 and toggle link 120 out of alignment. The friction in the toggle mechanism 119 is overcome when the load, which is being held back by the toggle, can act with a significant resultant force in a direction that is close to perpendicular to the vane 110 and toggle link 120, i.e., when one of the links reaches a predetermined angle from its rest position. This angle will vary with the amount of friction in the overall mechanism.

The vane pivot in the form of stub axles 111 (rotatable about axis B in FIGS. 20a and 20b) is located close to the stub pivots 121 (rotatable about axis C) of the toggle link 120. The vane 110 pivots downwards towards the base of the mouthpiece. This allows the toggle link 120 to be designed in a way that allows the actuation arm 130 to continue past the toggle link 120 once the mechanism is in the actuated position. This follow-through is required to ensure that the pMDI valve can reach total travel, and greatly improves the mechanism's robustness to dimensional variations in the pMDI valve and canister. This follow-through ensures that the vane 110 is held against the base of the mouthpiece but allows an actuating arm to pass by it (i.e., that allows "follow-through") in order to dispense medicament.

The rest position of the vane 110 is set at an angle (FIG. 20a) to help prevent airflow from leaking past the trigger mechanism. This also avoids any risk of clashing of the trigger mechanism with the vane 110, and therefore avoids adding unnecessary friction. At rest, the vane 110 provides a barrier to exhaled moisture and to bacteria and other undesirable entities in the exhaled breath: this is advantageous to protect the main parts of the inhaler should the patient unadvisedly exhale into it.

The Second Embodiment

Referring to FIGS. 22 to 27, a second pMDI 1060 in accordance with the invention is shown. The second pMDI is very similar to the first pMDI 60, and only the differences will be discussed here. Those differences lie in various components of the breath-actuated trigger mechanism 1100 (as compared to the mechanism 100).

Figure 23:
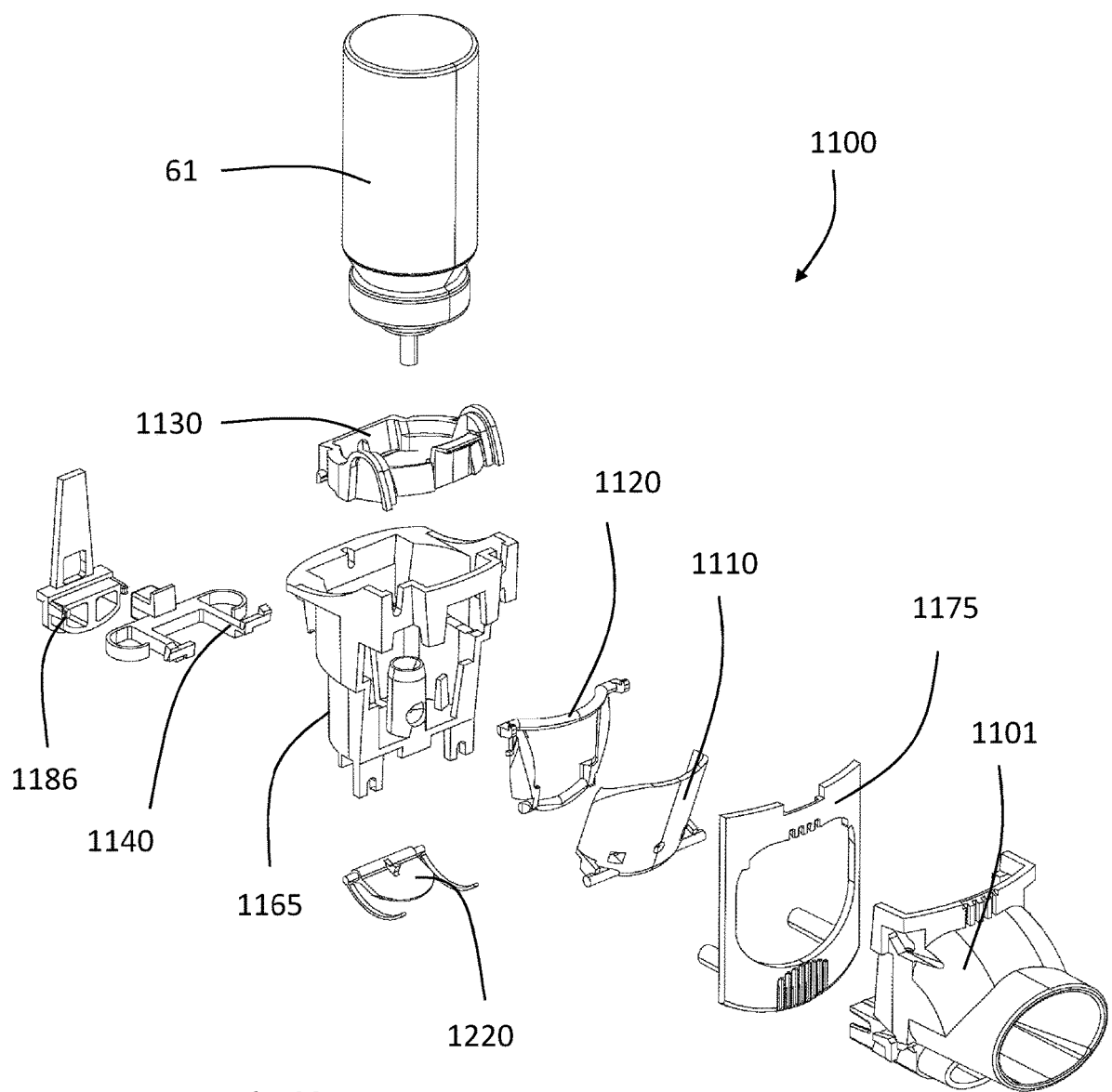
FIG. 23 is an exploded view of a subassembly of the pMDI inhaler of FIG. 22.

Referring to FIG. 23, the trigger system 1100 comprises a lower body component 1165, a trigger mechanism chassis 1101, a breath responsive member in the form of vane 1110, a toggle link 1120, an actuation arm 1130, a fascia component 1175, a flow governor support component 1186, a flow governor flap component 1220 and a button component 1140.

The trigger mechanism chassis 1101, the vane 1110, the toggle link 1120, the actuation arm 1130, the fascia component 1175 and the button component 1140 are substantially identical to those of the first pMDI 60 and as such will not be described in detail.

Figure 24:
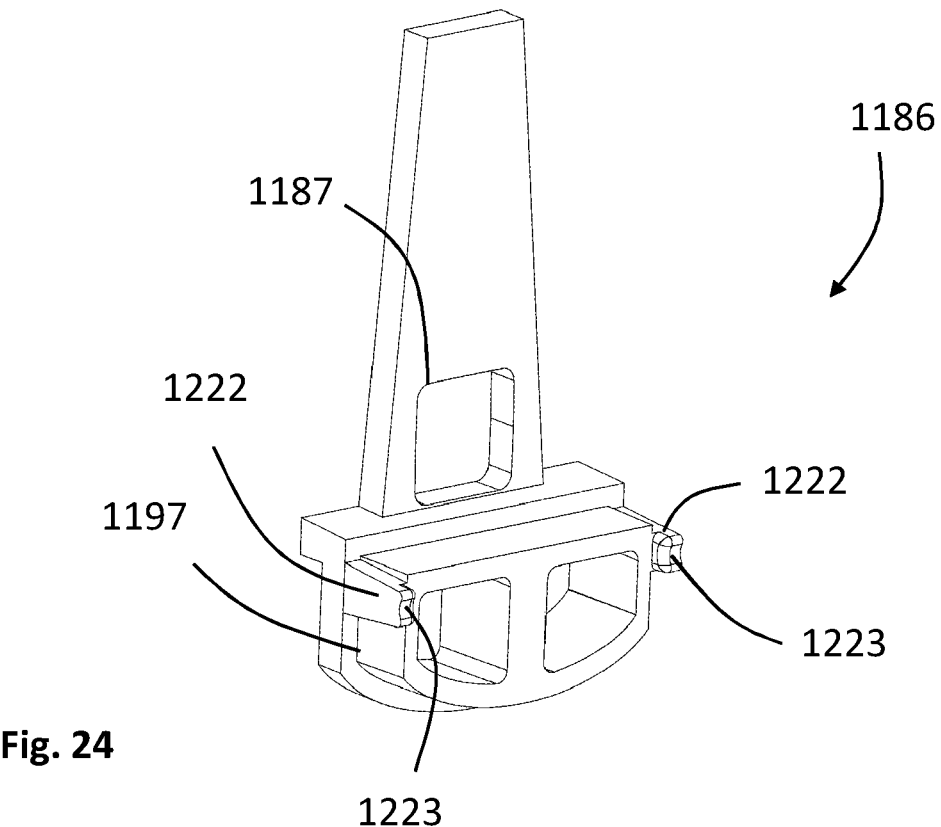
FIGS. 24 and 25 are perspective views of parts of the subassembly of FIG. 23.

FIG. 24 shows the flow governor support component 1186. The flow governor support component 1186 comprises a base 1197 having two opposed pivot receiving arms 1222. Each arm defines a concave pivot surface 1223 on a free end thereof. Additionally, the flow governor support component extends upwards at its back into a wall with an aperture 1187 in it. When the flow governor support component 1186 is assembled on to the lower body component 1165, this aperture 1187 provides a location for a button to protrude for access by the patient.

Figure 25:
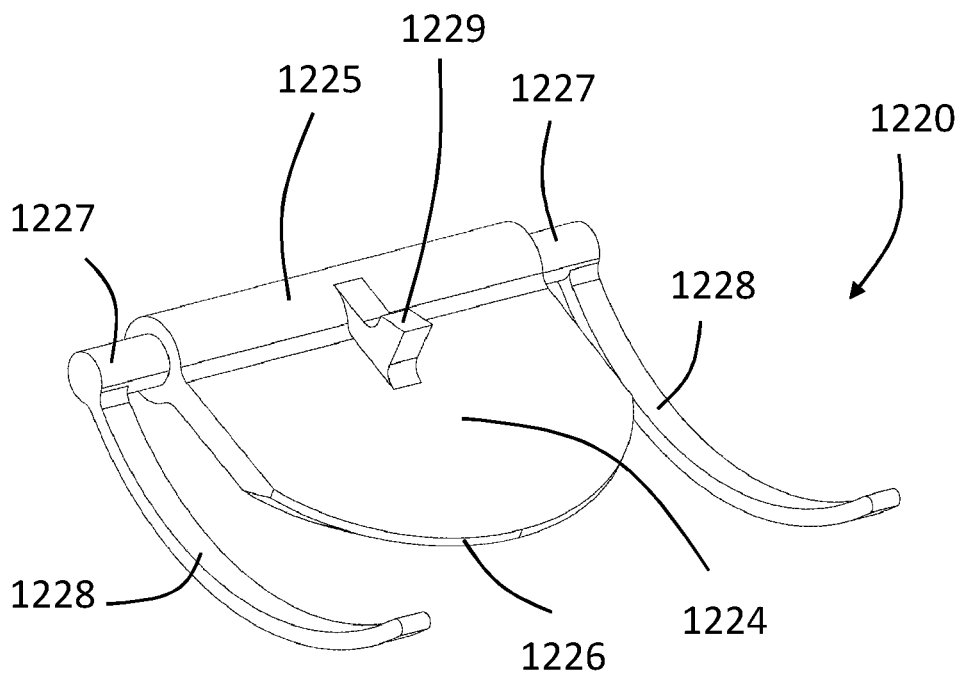

FIG. 25 shows the flow governor flap component 1220. The flow governor flap component 1220 comprises a flap 1224 having a mounted end 1225 and a free end 1226. At either side of the mounted end 1225 there are provided two opposing stub shafts 1227 each of which has a curved, resilient leaf spring member 1228 extending therefrom. A stop member 1229 extends from the face of the flap 1224.

Assembly

Figure 26:
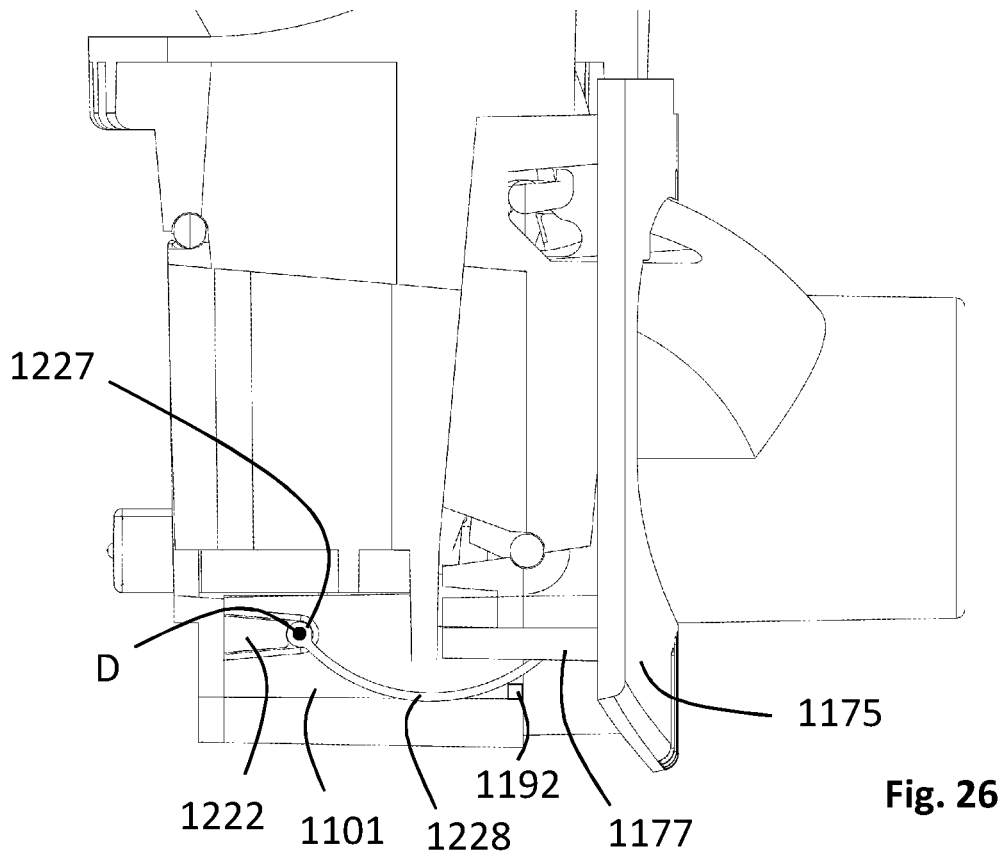
FIG. 26 is a side view of part of the pMDI inhaler of FIG. 22.
Figure 27:
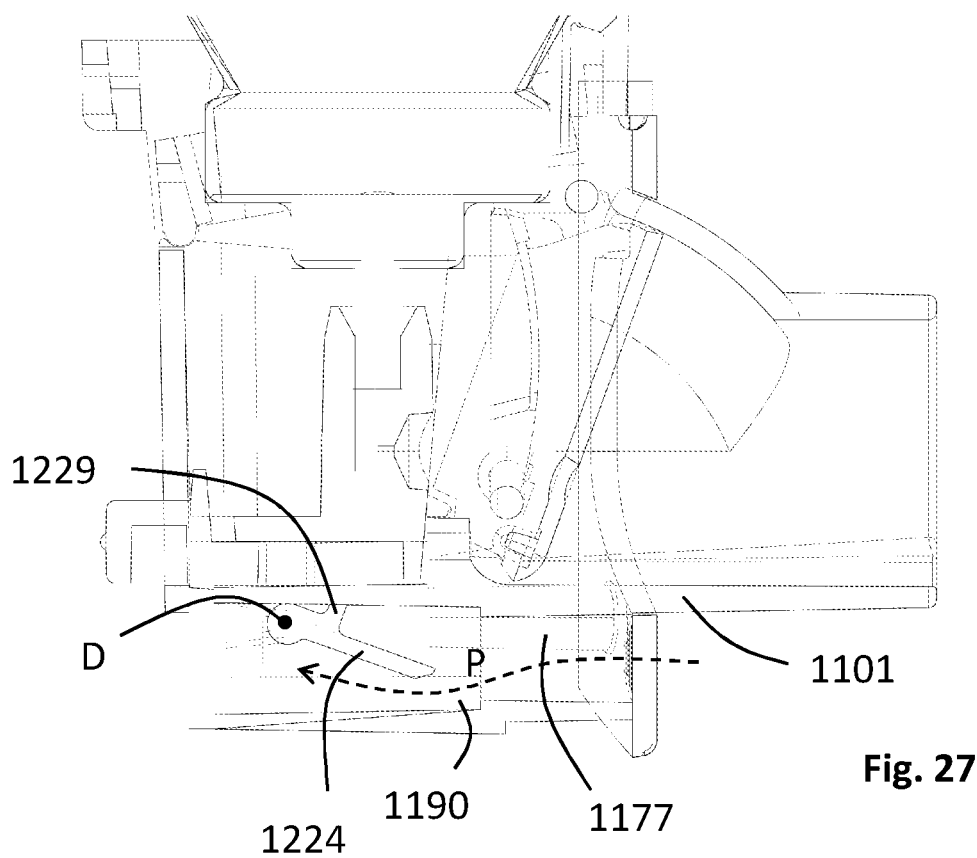
FIG. 27 is a section view of part of the pMDI inhaler of FIG. 22.

FIGS. 26 and 27 show the assembled trigger system 1100 from the side (FIG. 26) and in section (FIG. 27). The flap component 1220 is rotatably received against the flow governor support component 1186 for rotation about an axis D. The stub shafts 1227 bear against the concave pivot surfaces 1223 at the end of the pivot receiving arms 1222 and are held in position by engagement with the trigger mechanism chassis 1101. The spring arms 1228 bear against the mouthpiece component 1101 (or more specifically, respective outwardly directed pegs 1192 shown in FIG. 26) and are shown here in a loaded configuration.

Referring to FIG. 27, the flap 1224 sits within a flow governor passageway 1190 of the trigger mechanism chassis 1101. The stop member 1229 prevents the flap 1224 from sitting against the wall of the passageway, out of the air flow.

Operation

In the rest position (shown), a flow path P exists past the free end of the flap 1224. As the pressure drops past the flap (and on the lower surface thereof adjacent the flow path P), the flap 1224 starts to rotate in a clockwise direction about D, deforming the spring arms 1228. Thus, as flow rate is increased, the flow path cross section will decrease, decreasing flow rate in turn. Thus the flow is governed. The spring arms 1228 exert a generally anticlockwise (as drawn in FIG. 26) restorative force on the flap 1224 when it is rotated from its rest (no air flow) position.

Other than the aforementioned difference in the operation of the flow governor, the second pMDI 1060 operates in the same way as the first. Specifically, the actuation arm 1130 is configured to close an ungoverned bypass flow path upon triggering of the trigger system 1100.

As with the first embodiment, the second embodiment offers a largely ungoverned flow before triggering, and a governed flow after triggering.

The Third Embodiment

Figure 28:
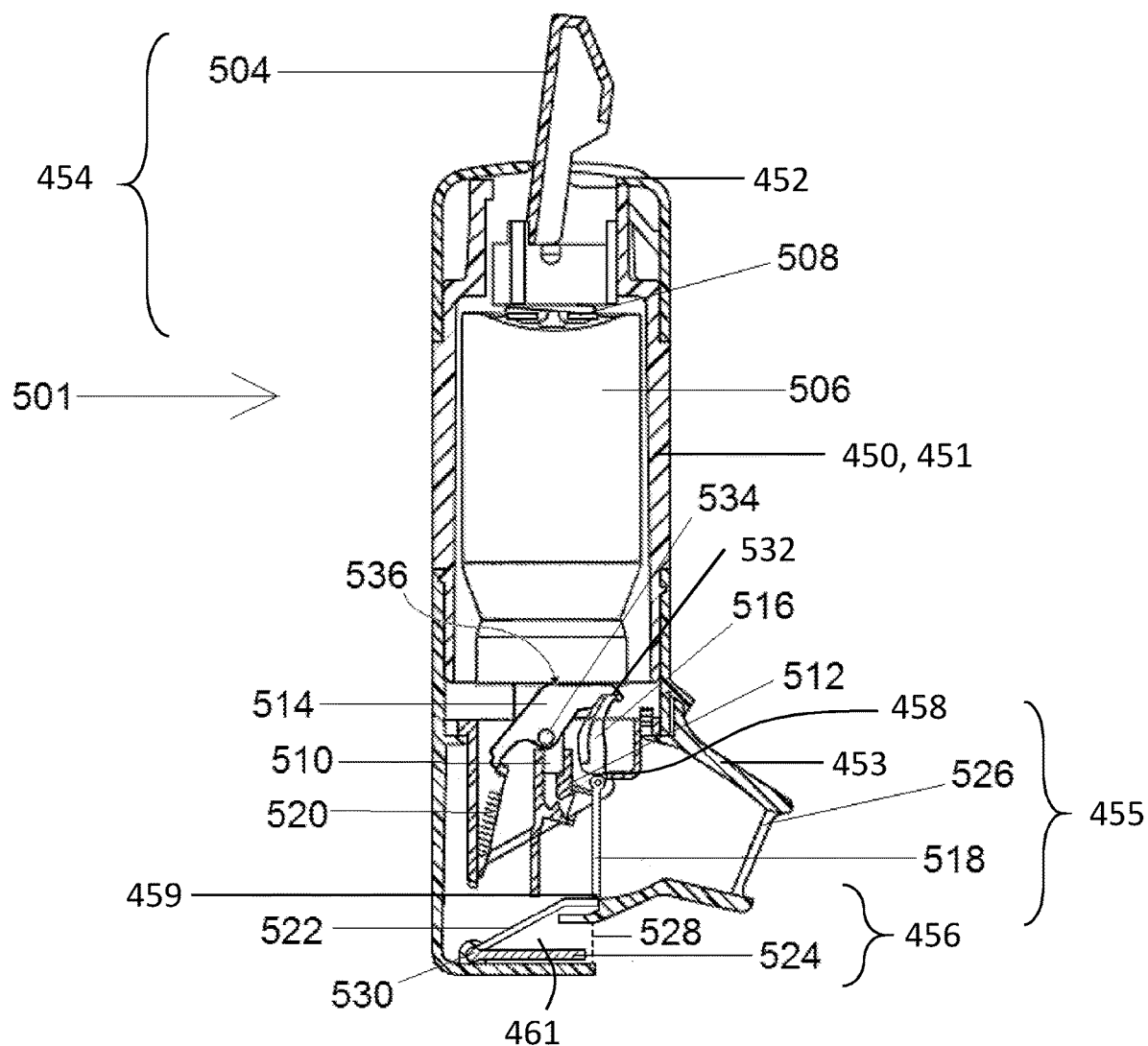
FIG. 28 is a section view of a third pMDI inhaler in accordance with the present invention in a first condition; and, FIG. 29 is a section view of a third pMDI inhaler in accordance with the present invention in a second condition.
Figure 29:
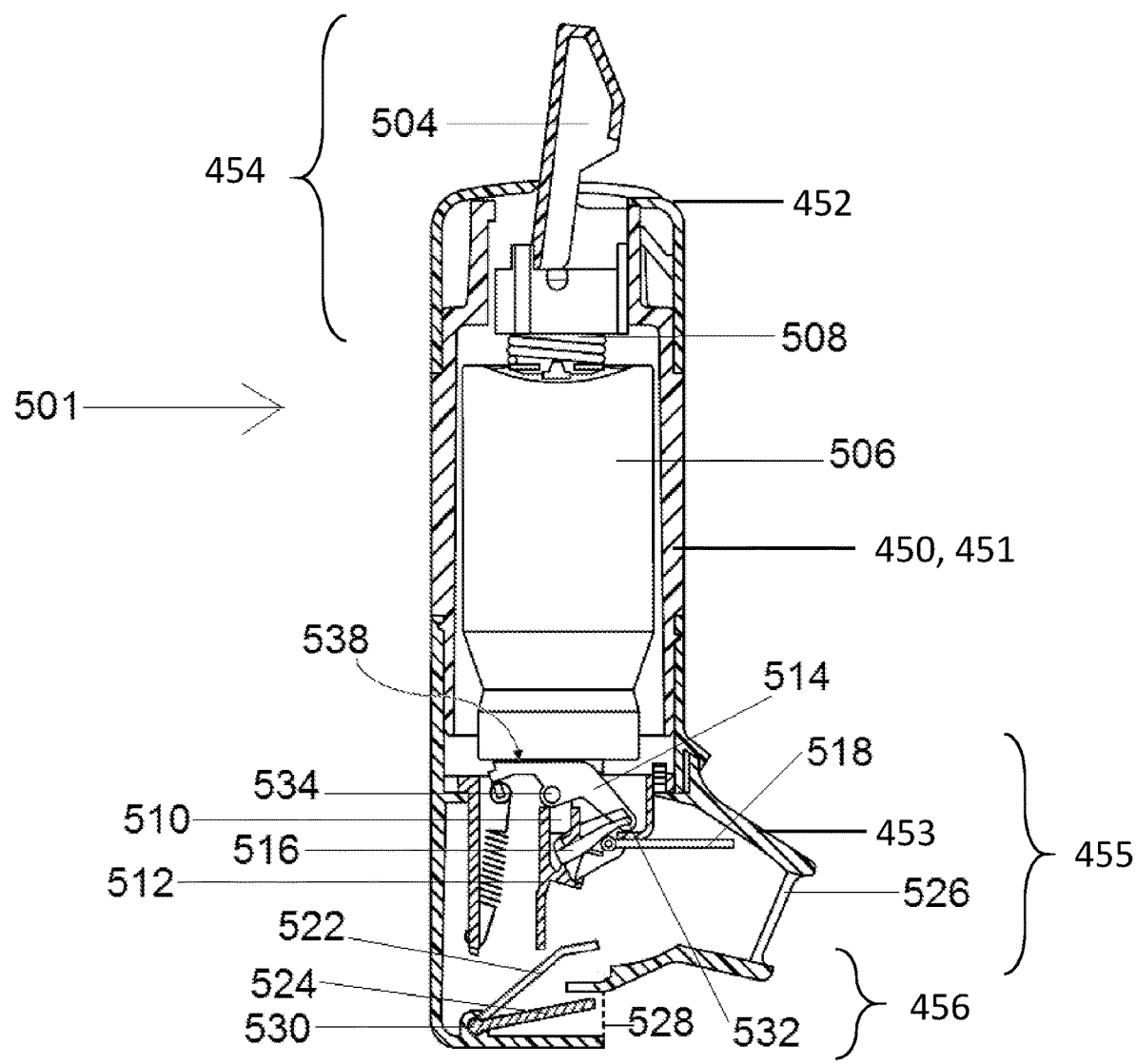

FIGS. 28 and 29 show side section views of a third breath-actuated pMDI inhaler 501 in accordance with the present invention.

The inhaler 501 generally comprises a housing 450 containing a pMDI canister 506. The canister 506 has a valve with a stem 510 protruding therefrom. The stem 510 is engaged into a nozzle block 512 in the housing 450.

The housing 450 further comprises a tubular sleeve portion 451 having an end 452 dimensioned to receive the inverted canister 506, and a portion in the form of a patient port 453 (e.g., in the form of a mouthpiece) that defines an inspiration orifice (or an air outlet) 526. Adjacent to the inspiration orifice 526 there is provided an air inlet 528 leading to a flow governor passage 461. The outlet 526 and the inlet 528 generally face in the same direction, such that the flow passage through the patient port 453 and the flow governor passage 461 are adjacent and generally parallel. It follows that the inspiration flow must almost reverse direction and flow past the nozzle block 512 when travelling from the inlet 528 to the outlet 526.

The inhaler 501 comprises a priming mechanism 454, a triggering mechanism 455 and a flow governor 456.

The priming mechanism 454 comprises a lever 504 protruding from the end 452 of the tubular sleeve portion 451 of the housing 450. The lever 504 is pivotable through about 90 degrees between a horizontal rest condition and a vertical primed condition (FIG. 28). The priming mechanism further comprises a caged compression spring 508 between the end of the lever 504 and the base of the inverted canister 506.

The triggering mechanism 455 comprises a rocker 514, a catch 516, a vane 518 and a tension spring 520. The rocker 514 is rotatably mounted about a pivot 534. The rocker defines a first and second canister abutment 536, 538. The rocker 514 is biased in an anti-clockwise direction as shown in FIGS. 28 and 29 by the tension spring 520.

The catch 516 is pivotably mounted to the rocker at a pivot 532 and defines a vane abutment 458.

The vane 518 comprises a governor abutment 459 at its free lower end.

The flow governor 456 comprises a flap 524 rotatable about a pivot 530. An arm 522 is connected to the flap 524 for rotation therewith.

Operation

In FIG. 28, the pMDI inhaler 501 is shown in a primed condition. In this condition, the lever 504 has been rotated to compress the spring 508 against the base of the canister 506. Because the canister is held in position by its abutment on the rocker abutment 536, the canister cannot move and the spring compresses to store energy.

The rocker 514 is prevented from pivoting clockwise on the rocker pivot 534, as it is constrained by the catch 516. The catch 516, in turn, is prevented from moving downward, or against rolling contact with the vane 518, by its vane abutment 458.

When the patient inhales on the mouthpiece to draw air through the outlet 526, air is drawn through the inlet 528. It will be noted that the flap 524 is held in an open, or lower, position by the fact that the arm is constrained by the governor abutment 459 of the vane 518. In other words, the arm 522 is held captive against the bottom edge of the vane 518, so the flap 524 is unable to raise at this stage.

As the pressure at the outlet 526 decreases, the vane rotates in an anti-clockwise sense.

FIG. 29 shows the breath-actuated inhaler 501 in a fired condition. Lever 504 is still raised. The rolling contact of the top of the vane 518 with the vane abutment 458 of the catch 516 has caused the catch to slip off the top of vane and move downwards, allowing the rocker 514 to rotate clockwise. Movement of the rocker allows the canister 506 to move downwards under the force of the spring 508 and to compress the stem 510 into the canister. The resulting flow of medicament passes into the nozzle block 512 towards the fluid outlet 526.

The canister 506 now rests on the second abutment 538 of the rocker, which is closer to the rocker pivot 534 than the first abutment 536.

Rotation of the vane 518 (and hence movement of the vane's governor abutment) makes it possible for the arm 522 of the governor 456 to rise under the influence of the Bernoulli forces created by the air flow past the upper surface of the flap 524. This, in turn, permits movement of the flap 524, leading to the air flow through the inlet 528 being governed.

The third embodiment offers an ungoverned flow before triggering, and a governed flow after triggering.

When the patient's inhalation eases off, the flap 524 returns to its rest position under gravity (this may also be achieved by employing a spring with very low force). Similarly, the vane 518 can return to the vertical position, again trapping the connected arm 522.

Variations

Variations fall within the scope of the present invention.

In both the first and second embodiments, the bypass flow path F2 is completely blocked in the triggered condition. It will be noted that partial blocking or occlusion of the bypass flow path will also work to the desired effect, although complete blocking is preferable.

Similarly, in the third embodiment, the flow governor is shown to be completely immobilised in the pre-triggered condition. It will be understood that the movement of the flow governor member may instead be partially constrained: i.e., a limited degree of movement may be permitted.

In both cases, the important thing is that the cross-section of governed flow (i.e., that over which the governor can act) is increased from the pre-triggered to the post-triggered condition.

The invention claimed is:

1. An inhaler comprising:
    a breath actuated trigger mechanism reactive to an inhalation flow to trigger the release of a substance to be inhaled into the inhalation flow;
    a first fluid flow path within the inhaler carrying part of the inhalation flow;
    a flow governor arranged to govern inhalation flow through the first fluid flow path; and, a second fluid flow path within the inhaler carrying part of the inhalation flow, the second fluid flow path bypassing the flow governor;

in which triggering the trigger mechanism reduces or blocks flow through the second fluid flow path, in which the second flow path is at least partially blocked by a part of the trigger mechanism after triggering.

2. An inhaler according to claim 1, in which the trigger mechanism comprises an actuation member configured to support a canister in a pre-triggered position, which actuation member moves to a post-triggered position upon triggering to thereby at least partially block the second flow path.

3. An inhaler according to claim 2, in which the actuation member defines a valve member, and the inhaler comprises a valve seat for the second flow path, in which in the pre-triggered position of the actuation member the valve member and valve seat are spaced apart, and in the post-triggered position the valve member abuts the valve seat.

4. An inhaler according to claim 3, in which the valve member and valve seat are shaped to mate upon engagement.

5. An inhaler according to claim 4, in which the valve member is convex, and the valve seat is concave.

6. An inhaler according to claim 2, in which the trigger mechanism comprises a toggle mechanism for selectively permitting movement of the actuation member from its pre-triggered position to its post-triggered position.

7. An inhaler according to claim 6, in which the toggle mechanism comprises a vane positioned in the inhalation flow, the vane being moveable upon inhalation of a user to move the toggle mechanism between a primed condition in which the actuation member is maintained in its pre-triggered position by cooperation with the toggle mechanism and its post-triggered condition in which the toggle mechanism permits movement of the actuation member.

8. An inhaler according to claim 2, in which the actuation member is an actuation arm that is pivotable about a pivot axis.

9. An inhaler according to claim 8, in which the actuation arm is configured to at least partially block the second flow path at a position on the opposite side of the canister to the pivot axis.

10. An inhaler according to claim 1, in which the first flow path has a first flow inlet defined on the inhaler, and the second flow path has a second flow inlet defined on the inhaler, distinct from the first.

11. An inhaler according to claim 10, comprising a flow outlet for carrying an inhalation flow, in which the first and second flow inlets are adjacent the flow outlet.

12. An inhaler according to claim 10, in which the first and second flow inlets are on opposites sides of the flow outlet.

13. An inhaler according to claim 11, comprising a cover member configured to selectively cover the first and second flow inlets and the flow outlet.

14. An inhaler according to claim 1, in which the trigger mechanism is positioned downstream of the second flow path.

15. An inhaler according to claim 14, in which the trigger mechanism when it triggers reduces or blocks flow through the second fluid flow path upstream of a canister outlet.

* * * * *